United States Patent [19]

Panetta

[11] Patent Number: 5,356,917

[45] Date of Patent: Oct. 18, 1994

[54] ARYL-SUBSTITUTED RHODANINE DERIVATIVES

[75] Inventor: Jill A. Panetta, Zionsville, Ind.

[73] Assignee: Eli Lilly and Company, Indianapolis, Ind.

[21] Appl. No.: 111,226

[22] Filed: Aug. 24, 1993

Related U.S. Application Data

[63] Continuation of Ser. No. 839,693, Feb. 20, 1992, abandoned, which is a continuation of Ser. No. 504,147, Apr. 3, 1990, abandoned, which is a continuation-in-part of Ser. No. 335,063, Apr. 7, 1989, abandoned, which is a continuation-in-part of Ser. No. 304,919, Feb. 1, 1989, abandoned, which is a continuation of Ser. No. 114,278, Oct. 27, 1987, abandoned, which is a continuation of Ser. No. 869,488, Jun. 2, 1986, abandoned, which is a continuation-in-part of Ser. No. 764,160, Aug. 9, 1985, abandoned.

[51] Int. Cl.$^5$ .................. C07D 277/14; A61K 31/425
[52] U.S. Cl. ..................................... 514/369; 548/183; 548/186; 548/187; 549/30
[58] Field of Search .......................... 514/364; 549/30; 548/183, 186, 187

[56] References Cited

U.S. PATENT DOCUMENTS

| | | | |
|---|---|---|---|
| 4,287,200 | 2/1981 | Kawamatsu et al. | 424/270 |
| 4,376,777 | 3/1983 | Kawamatsu et al. | 424/270 |
| 4,387,101 | 6/1983 | Kawamatsu et al. | 424/270 |
| 4,461,902 | 7/1984 | Kawamatsu et al. | 548/183 |
| 4,464,382 | 8/1984 | Tanouchi et al. | 424/270 |
| 4,636,516 | 1/1987 | Kubo et al. | 514/365 |

FOREIGN PATENT DOCUMENTS

| | | | |
|---|---|---|---|
| 59090 | 9/1982 | European Pat. Off. | C07D 233/64 |
| 47109 | 3/1983 | European Pat. Off. | C07D 417/14 |
| 204964 | 12/1986 | European Pat. Off. | C07D 207/38 |
| 211670 | 2/1987 | European Pat. Off. | A61K 31/39 |
| 343643 | 5/1989 | European Pat. Off. | A61K 31/41 |
| 1038050 | 9/1958 | Fed. Rep. of Germany . | |

OTHER PUBLICATIONS

Poster Presentation, National ACS Meeting, Sep. 25–30, 1988.
Abstract of Poster Presentation for National ACS Meeting, Sep. 25–30, 1988.
Extend Abstract of Poster Presentation for National ACS Meeting, Sep. 25–30, 1988.
Patent Abstracts of Japan, 11(206), (C–433) [2653] (1987), abstracting JP 60-167999.
Patent Abstracts of Japan, 11(232), (C–437) [2679] (1987), abstracting JP 60-184085.
Teuber et al., *Liebigs Ann. Chem.*, 757 (1978).
Patent Abst. of Japan, 5(168), (C–77) [840] 1981, abstracting JP 56-97277.
Ito et al., *Agr. Biol. Chem.*, 29(8), 728 (1965).
Derwent 87–076383/11, abstracting J6 2029-579-A (1987).
Isomura et al., *Chem. Pharm. Bul.*, 32(1), 152 (1984).
Hidaka et al., *Japan J. Pharmacol.*, 36(77) (1984).
Derwent 84–213508/35, abstracting Australian Patent 8423-287 (1984).
Derwent 85–113078/19, abstracting Japanese J6 0054-315-A (1985).
Katsumi et al., *Chem. Pharm. Bul.*, 35(4), 1619 (1986).

*Primary Examiner*—Robert Gerstl
*Attorney, Agent, or Firm*—Douglas J. Taylor

[57] ABSTRACT

Provided are certain aryl-substituted rhodanine derivatives, treatment methods and pharmaceutical formulations thereof.

90 Claims, No Drawings

ARYL-SUBSTITUTED RHODANINE DERIVATIVES

This application is a continuation of co-pending application Ser. No. 07/839,693, filed Feb. 20, 1992; now abandoned which is a continuation of application Ser. No. 07/504,147, filed Apr. 3, 1990, now abandoned; which is a continuation-in-part of application Ser. No. 07/335,063, filed Apr. 7, 1989, now abandoned; which is a continuation-in-part of application Ser. No. 07/304,919, filed Feb. 1, 1989, now abandoned; which is a continuation of application Ser. No. 07/114,278, filed Oct. 27, 1987, now abandoned; which is a continuation of application Ser. No. 06/869,488, filed Jun. 2, 1986, now abandoned; which is a continuation-in-part of application Ser. No. 06/764,160, filed Aug. 9, 1985, now abandoned.

SUMMARY OF THE INVENTION

This invention provides compounds of the formula (I)

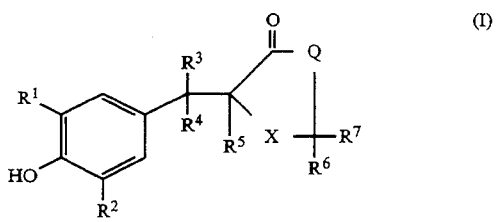

wherein:

$R^1$ and $R^2$ are each independently hydrogen, $C_1$-$C_6$ alkyl or $C_1$-$C_6$ alkoxy or

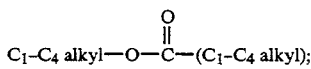

$R^3$ is hydrogen or $C_1$-$C_6$ alkyl;

$R^4$ and $R^5$ are each hydrogen, or when taken together form a bond;

$R^6$ and $R^7$ are each hydrogen or when taken together are =S, or when one of $R^6$ or $R^7$ is hydrogen, the other is —OH or —SCH$_3$;

X is

where m is 0, 1 or 2; and

Q is —CH$_2$—, —O— or NR$^8$ where $R^8$ is hydrogen, $C_1$-$C_6$ alkyl, $C_3$-$C_8$ cycloalkyl, $C_2$-$C_6$ alkenyl, —SO$_2$CH$_3$ or —(CH$_2$)$_n$—Y, where n is an integer from 0 to 3, both inclusive, and Y is cyano OR$^9$,

tetrazolyl, —NR$^{11}$R$^{12}$, —SH, —S(C$_1$-C$_4$ alkyl) or

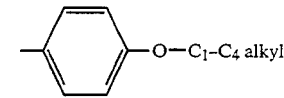

where $R^9$ is hydrogen, $C_1$-$C_4$ alkyl, tosyl or

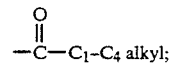

$R^{10}$ is $C_1$-$C_4$ alkyl, $C_1$-$C_4$ alkoxy or —NH$_2$; $R^{11}$ and $R^{12}$ are each independently hydrogen, $C_1$-$C_6$ alkyl, $C_2$-$C_6$ alkenyl, $C_2$-$C_6$ alkynyl, —(CH$_2$)$_q$OH, —(CH$_2$)$_q$—N(C$_1$-C$_4$ alkyl)$_2$, —(CH$_2$)$_q$—S(C$_1$-C$_4$ alkyl) or

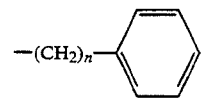

where q is an integer from 1 to 6, both inclusive, and n is as defined above; or $R^{11}$ and $R^{12}$ taken together form a morpholinyl, piperidinyl, piperazinyl or an N-methylpiperazinyl ring;

with the proviso that when $R^3$ is hydrogen and $R^4$ and $R^5$ taken together form a bond and Q is NR$^8$ (and $R^8$ is hydrogen), $R^6$ and $R^7$ may not be =S.

In addition to the compounds of Formula I, this invention also provides a method of treating inflammation and arthritis in a mammal in need of such treatment which comprises administering to said mammal a therapeutically effective amount of a compound of formula II

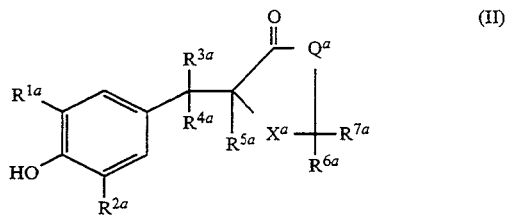

wherein:

$R^{1a}$ and $R^{2a}$ are each independently hydrogen, $C_1$-$C_6$ alkyl, $C_1$-$C_6$ alkoxy or

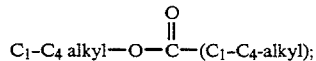

$R^{3a}$ is hydrogen or $C_1$-$C_6$ alkyl;

$R^{4a}$ and $R^{5a}$ are each hydrogen or when taken together form a bond;

$R^{6a}$ and $R^{7a}$ are each hydrogen or when taken together are =S, or when one of $R^{6a}$ and $R^{7a}$ is hydrogen the other is —OH or —SCH$_3$;

$X^a$ is

where m is as defined for formula I; and $Q^a$ is —$CH_2$—, —O— or $NR^{8a}$ where $R^{8a}$ is hydrogen, $C_1$-$C_6$ alkyl, $C_3$-$C_8$ cycloalkyl, $C_2$-$C_6$ alkenyl, —$SO_2CH_3$ or —$(CH_2)_n$—$Y^a$, where n is as defined for formula I and $Y^a$ is cyano, $OR^{9a}$,

tetrazolyl, —$NR^{11a}R^{12a}$, SH, —$S(C_1$-$C_4$ alkyl) or

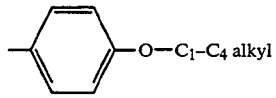

where $R^{9a}$ is hydrogen, $C_1$-$C_4$ alkyl, or

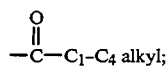

$R^{10a}$ is $C_1$-$C_4$ alkyl, $C_1$-$C_4$ alkoxy or —$NH_2$; $R^{11a}$ and $R^{12a}$ are each independently hydrogen, $C_1$-$C_6$ alkyl, $C_2$-$C_6$ alkenyl, $C_2$-$C_6$ alkynyl, —$(CH_2)_q$OH, —$(CH_2)_q$—$N(C_1$-$C_4$ alkyl)$_2$, —$(CH_2)_q$—$S(C_1$-$C_4$ alkyl) or

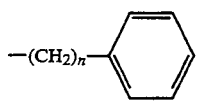

where n and q are as defined for formula I; or $R^{11a}$ and $R^{12a}$ taken together form a morpholinyl, piperidinyl, piperazinyl or an N-methylpiperazinyl ring.

According to a further aspect of the present invention, there is provided a pharmaceutical composition which comprises as active ingredient a compound of Formula II as defined above in association with one or more pharmaceutically acceptable diluents, excipients or carriers therefor.

Moreover, it has been discovered that compounds of formula III

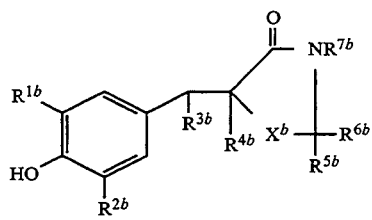

wherein:
$R^{1b}$ and $R^{2b}$ are each independently $C_1$-$C_6$ alkyl;
$R^{3b}$ and $R^{4b}$ are each hydrogen or when taken together form a bond;
$R^{5b}$ and $R^{6b}$ are each hydrogen or when taken together are =O;
$X^b$ is —$CH_2$— or

where m is as defined for formula I;
$R^{7b}$ is hydrogen, $C_1$-$C_6$ alkyl, or —$(CH_2)_n$—$Y^b$, where n is as defined for formula I and $Y^b$ is cyano, $OR^{8b}$,

—SH, —$S(C_1$-$C_4$ alkyl), tetrazolyl, —$NR^{10b}R^{11b}$ or

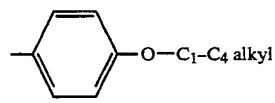

where $R^{8b}$ is hydrogen, $C_1$-$C_4$ alkyl, or

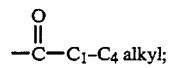

$R^{9b}$ is —$NH_2$ or —OH; and $R^{10b}$ and $R^{11b}$ are each independently hydrogen, $C_1$-$C_6$ alkyl, $C_2$-$C_6$ alkenyl or $C_2$-$C_6$ alkynyl;
are also useful for preventing ischemia-induced brain damage such as may be caused by strokes, for example. This invention, therefore, also provides a method for preventing ischemia-induced cell damage in mammals by administering to a mammal in need thereof an effective ischemia reducing amount of a compound of formula III.

Further, it has been found that the lifespan of dystrophic mice has been prolonged by the administration of certain compounds of the present invention. Accordingly, a method is also provided for the treatment of a dystrophic mammal by the administration of an effective amount of a compound of the formula (IV)

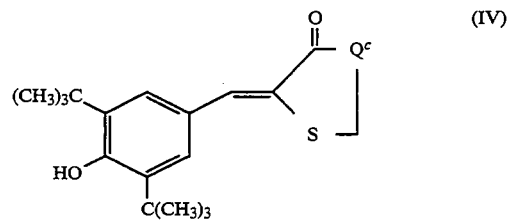

wherein:
$Q^c$ is —O— or $NR^{7c}$, where $R^{7c}$ is hydrogen, $C_1$-$C_6$ alkyl, $NR^{8c}R^{9c}$ or —$(CH_2)_n$—OH, where $R^{8c}$ and $R^{9c}$ each independently hydrogen or $C_1$-$C_4$ alkyl and n is as defined for formula I.

DETAILED DESCRIPTION OF THE INVENTION

As used herein, the term "$C_1$-$C_6$ alkyl" refers to straight and branched chain aliphatic radicals of 1 to 6 carbon atoms, both inclusive, such as methyl, ethyl, propyl, isopropyl, butyl, isobutyl, sec-butyl, tert-butyl, n-pentane, isopentane, n-hexane, isohexane and the like. The term "$C_1$-$C_6$ alkyl" includes within its definition the term "$C_1$-$C_4$ alkyl".

The term "$C_1$-$C_6$ alkoxy" refers to the alkyl radicals of 1 to 6 carbon atoms, both inclusive, attached to the remainder of the molecule by oxygen and includes methoxy, ethoxy, propoxy, isopropoxy, butoxy, isobutoxy, sec-butoxy, tert-butoxy, pentoxy, hexoxy and the like. The term "$C_1$-$C_6$ alkoxy" includes within its definition the term "$C_1$-$C_4$ alkoxy".

The term "$C_2$-$C_6$ alkenyl" refers to straight and branched chain radicals of 2 to 6 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene and the like.

The term "$C_2$-$C_6$ alkynyl" refers to straight and branched chain radicals of 2 to 6 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne and the like.

The term "$C_3$-$C_8$ cycloalkyl" refers to saturated alicyclic rings of 3 to 8 carbon atoms, both inclusive, such as cyclopropyl, methylcyclopropyl, cyclobutyl, cyclopentyl, cyclohexyl and cyclooctyl.

Compounds of formula I wherein $R^1$ and $R^2$ are each independently hydrogen, $C_1$-$C_6$ alkoxy,

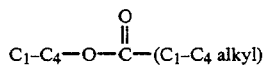

or $C_1$-$C_6$ alkyl, except for 1,1-dimethylethyl, and $R^3$, $R^4$, $R^5$, $R^6$, $R^7$, X, m and Q are as defined for formula I are preferred. Of this preferred group of compounds, those compounds wherein $R^1$ and $R^2$ are each independently hydrogen, $C_1$-$C_6$ alkoxy,

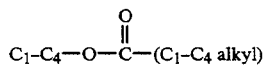

or a methyl, ethyl, hexyl, isohexyl or neohexyl group and $R^3$, $R^4$, $R^5$, $R^6$, $R^7$, X, m and Q are as defined for formula I are particularly preferred.

Furthermore, compounds of formula I wherein $R^1$ and $R^2$ are each $C_1$-$C_6$ alkyl; $R^3$ is hydrogen; $R^4$ and $R^5$ taken together form a bond; $R^6$ and $R^7$ are each hydrogen; X is

where m is O; and Q is —O— or $NR^8$, where $R^8$ is as defined for formula I, are also preferred. Of this preferred group of compounds, those compounds wherein $R^1$ and $R^2$ are each 1,1-dimethylethyl; $R^3$ is hydrogen; $R^4$ and $R^5$ taken together form a bond; $R^6$ and $R^7$ are each hydrogen; X is

where m is O; and Q is $NR^8$, where $R^8$ is hydrogen, $C_1$-$C_6$ alkyl or —$(CH_2)_n$—Y, where n and Y are as defined for formula I, are particularly preferred.

Another preferred subgenus of the compounds of formula I includes compounds wherein $R^1$ and $R^2$ are each independently other than

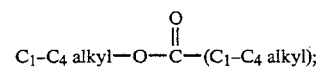

$R^8$ is other than $C_2$-$C_6$ alkenyl; Y is other than —SH or —S($C_1$-$C_4$ alkyl); $R^9$ is other than tosyl; and $R^{11}$ and $R^{12}$ are other than $C_2$-$C_6$ alkenyl or $C_2$-$C_6$ alkynyl. Preferred subgenuses of the above-mentioned subgenus include compounds of formula I wherein $R^1$ and $R^2$ are each independently hydrogen, $C_1$-$C_6$ alkoxy or $C_1$-$C_6$ alkyl, except for 1,1-dimethylethyl, and $R^3$, $R^4$, $R^5$, $R^6$, $R^7$, X, m and Q are as defined for formula I (with the substituent definitions limited in the manner noted above); or $R^1$ and $R^2$ are each independently hydrogen, $C_1$-$C_6$ alkoxy or a methyl, ethyl, hexyl, isohexyl or neohexyl group and $R^3$, $R^4$, $R^5$, $R^6$, $R^7$, X, m and Q are as defined for formula I (with the substituent definitions also limited in the manner noted above).

A further preferred subgenus of the above-mentioned subgenus includes compounds of formula I wherein $R^1$ and $R^2$ are each $C_1$-$C_6$ alkyl; $R^3$ is hydrogen; $R^4$ and $R^5$ taken together form a bond; $R^6$ and $R^7$ are each hydrogen; X is

where m is O; and Q is —O— or $NR^8$, where $R^8$ is as defined for formula I and is as limited in the manner noted above. Of this preferred subgenus of compounds, those compounds wherein $R^1$ and $R^2$ are each 1,1-dimethylethyl; $R^3$ is hydrogen; $R^4$ and $R^5$ taken together form a bond; $R^6$ and $R^7$ are each hydrogen; X is

where m is O; and Q is $NR^8$, where $R^8$ is hydrogen, $C_1$-$C_6$ alkyl or —$(CH_2)_n$—Y, where n and Y are as defined for formula I and are as limited in the manner noted above, are particularly preferred.

A most preferred group of compounds of formula I includes compounds wherein $R^1$ and $R^2$ are each 1,1-dimethylethyl; $R^3$ is hydrogen; $R^4$ and $R^5$ are each hydrogen, or when taken together form a bond; $R^6$ and $R^7$ are each hydrogen, or when taken together are=S; X is

where m is O; and Q is $NR^8$, where $R^8$ is hydrogen or $C_1$-$C_4$ alkyl.

In the method of treating inflammation and arthritis, as well as the pharmaceutical compositions of the present invention, the following compounds of formula II are preferred.

Compounds of formula II wherein $R^{1a}$ and $R^{2a}$ are each independently hydrogen, $C_1$-$C_6$ alkoxy,

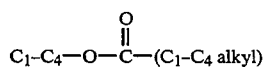

or $C_1$-$C_6$ alkyl, except for 1,1-dimethylethyl, and $R^{3a}$, $R^{4a}$, $R^{5a}$, $R^{6a}$, $R^{7a}$, $X^a$, m and $Q^a$ are as defined for formula II are preferred. Of this preferred group of compounds, those compounds wherein $R^{1a}$ and $R^{2a}$ are each independently hydrogen, $C_1$-$C_6$ alkoxy,

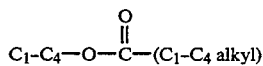

or a methyl, ethyl, hexyl, isohexyl or neohexyl group and $R^{3a}$, $R^{4a}$, $R^{5a}$, $R^{6a}$, $R^{7a}$, $X^a$, m and $Q^a$ are as defined for formula I are particularly preferred.

Furthermore, compounds of formula II wherein $R^{1a}$ and $R^{2a}$ are each $C_1$-$C_6$ alkyl; $R^{3a}$ is hydrogen; $R^{4a}$ and $R^{5a}$ taken together form a bond; $R^{6a}$ and $R^{7a}$ are each hydrogen;
$X^a$ is

where m is O; and $Q^a$ is —O— or $NR^{8a}$ where $R^{8a}$ is as defined for formula II, are also preferred. Of this preferred group of compounds, those compounds wherein $R^{1a}$ and $R^{2a}$ are each 1,1-dimethylethyl; $R^{3a}$ is hydrogen; $R^{4a}$ and $R^{5a}$ taken together form a bond; $R^{6a}$ and $R^{7a}$ are each hydrogen;
$X^a$ is

where m is O; and $Q^a$ is $NR^{8a}$, where $R^{8a}$ is hydrogen, $C_1$-$C_6$ alkyl or —$(CH_2)_n$—Y, where n and Y are as defined for formula II, are particularly preferred.

Another preferred subgenus of the compounds of formula II includes compounds wherein $R^{1a}$ and $R^{2a}$ are each independently other than

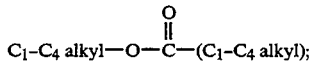

$R^{8a}$ is other than $C_2$-$C_6$ alkenyl; Y is other than —SH or —S($C_1$-$C_4$ alkyl); $R^{9a}$ is other than tosyl; and $R^{11a}$ and $R^{12a}$ are other than $C_2$-$C_6$ alkenyl or $C_2$-$C_6$ alkynyl. Preferred subgenuses of the above-mentioned subgenus include compounds of formula II wherein $R^{1a}$ and $R^{2a}$ are each independently hydrogen, $C_1$-$C_6$ alkoxy or $C_1$-$C_6$ alkyl, except for 1 1-dimethylethyl, and $R^{3a}$, $R^{4a}$, $R^{5a}$, $R^{6a}$, $R^{7a}$, $X^a$, m and $Q^a$ are as defined for formula II (with the substituent definitions limited in the manner noted above); or $R^{1a}$ and $R^{2a}$ are each independently hydrogen, $C_1$-$C_6$ alkoxy or a methyl, ethyl, hexyl, isohexyl or neohexyl group and $R^{3a}$, $R^{4a}$, $R^{5a}$, $R^{6a}$, $R^{7a}$, $X^a$, m and $Q^a$ are as defined for formula II (with the substituent definitions also limited in the manner noted above).

A further preferred subgenus of the above-mentioned subgenus includes compounds of formula II wherein $R^{1a}$ and $R^{2a}$ are each $C_1$-$C_6$ alkyl; $R^{3a}$ is hydrogen; $R^{4a}$ and $R^{5a}$ taken together form a bond; $R^{6a}$ and $R^{7a}$ are each hydrogen;
$X^a$ is

where m is O; and $Q^a$ is —O— or $NR^{8a}$, where $R^{8a}$ is as defined for formula II and is as limited in the manner noted above. Of this preferred subgenus of compounds, those compounds wherein $R^{1a}$ and $R^{2a}$ are each 1,1-dimethylethyl; $R^{3a}$ is hydrogen; $R^{4a}$ and $R^{5a}$ taken together form a bond; $R^{6a}$ and $R^{7a}$ are each hydrogen;
$X^a$ is

where m is O; and $Q^a$ is $NR^{8a}$, where $R^{8a}$ is hydrogen, $C_1$-$C_6$ alkyl or —$(CH_2)_n$—$Y^a$, where n and $Y^a$ are as defined for formula II and are as limited in the manner noted above, are particularly preferred.

A most preferred group of compounds of formula II includes compounds wherein $R^{1a}$ and $R^{2a}$ are each 1,1-dimethylethyl; $R^{3a}$ is hydrogen; $R^{4a}$ and $R^{5a}$ are each hydrogen, or when taken together form a bond; $R^{6a}$ and $R^{7a}$ are each hydrogen, or when taken together are=S;
$X^a$ is

where m is O; and $Q^a$ is $NR^{8a}$, where $R^{8a}$ is hydrogen or $C_1$-$C_4$ alkyl.

Compounds of formula III wherein $R^{1b}$ and $R^{2b}$ are each independently $C_1$-$C_6$ alkyl, except for 1,1-dimethylethyl, and $R^{3b}$, $R^{4b}$, $R^{5b}$, $R^{6b}$, $X^b$, m and $R^{7b}$ are as defined for formula III are preferred for use in the prevention of ischemia-induced cell damage in mammals. Of this preferred group of compounds of formula III, those compounds wherein $R^{1b}$ and $R^{2b}$ are each independently a methyl, ethyl, hexyl, isohexyl or neohexyl group and $R^{3b}$, $R^{4b}$, $R^{5b}$, $R^{6b}$, $X^b$, m and $R^{7b}$ are as defined for formula III, are particularly preferred.

Furthermore, compounds of formula III wherein $R^{1b}$ and $R^{2b}$ are each independently $C_1$-$C_6$ alkyl; $R^{3b}$ and $R^{4b}$ taken together form a bond; $R^{5b}$ and $R^{6b}$ are each hydrogen;
$X^b$ is

where m is O; and $R^{7b}$ is as defined for formula III are also preferred for use in the prevention of ischemia-induced cell damage in mammals. Of this preferred group of compounds, those compounds wherein $R^{1b}$ and $R^{2b}$ are each 1,1-dimethylethyl; $R^{3b}$ and $R^{4b}$ taken together form a bond; $R^{5b}$ and $R^{6b}$ are each hydrogen;
$X^b$ is

where m is O; and $R^{7b}$ is as defined for formula III are particularly preferred.

Another preferred subgenus of the compounds of formula III which can be used in the prevention of ischemia-induced cell damage in mammals includes compounds of formula III wherein in the definition of $R^{7b}$, $Y^b$ is other than —SH or —S($C_1$-$C_4$ alkyl) and $R^{10b}$ and $R^{11b}$ are other than $C_2$-$C_6$ alkenyl or $C_2$-$C_6$ alkynyl. Preferred subgenuses of the above-mentioned subgenus include compounds of formula III wherein $R^{1b}$ and $R^{2b}$ are each independently $C_1$-$C_6$ alkyl, except for 1,1-dimethylethyl, and $R^{3b}$, $R^{4b}$, $R^{5b}$, $R^{6b}$ and $R^{7b}$ are as defined for formula III (with the definition of $R^{7b}$ limited in the manner noted above); or $R^{1b}$ and $R^{2b}$ are each independently a methyl, ethyl, hexyl, isohexyl or neohexyl group and $R^{3b}$, $R^{4b}$, $R^{5b}$, $R^{6b}$ and $R^{7b}$ are as defined for formula III (with the definition of $R^{7b}$ limited in the manner noted above).

A further preferred subgenus of the above-mentioned subgenus includes compounds of formula III wherein $R^{1b}$ and $R^{2b}$ are each independently $C_1$-$C_6$ alkyl; $R^{3b}$ and $R^{4b}$ taken together form a bond; $R^{5b}$ and $R^{6b}$ are each hydrogen;
$X^b$ is

where m is O; and $R^{7b}$ is as defined for formula III and is limited in the manner noted above. Of this preferred subgenus of compounds, those compounds wherein $R^{1b}$ and $R^{2b}$ are each 1,1-dimethylethyl; $R^{3b}$ and $R^{4b}$ taken together form a bond; $R^{5b}$ and $R^{6b}$ are each hydrogen; $X^b$ is

where m is O; and $R^{7b}$ is a defined for formula III and is as limited in the manner noted above, are particularly preferred for use in the prevention of ischemia-induced cell damage in mammals.

A most preferred group of compounds of formula III which can be used in the prevention of ischemia-induced cell damage in mammals includes compounds wherein $R^{1b}$ and $R^{2b}$ are each 1 1-dimethylethyl; and $R^{3b}$ and $R^{4b}$ taken together form a bond; $R^{5b}$ and $R^{6b}$ are each hydrogen;
$X^b$ is

where m is O; and $R^{7b}$ is hydrogen or $C_1$-$C_4$ alkyl.

Compounds of the present invention include the following:

5-{[3,5-bis(1,1-dimethylethyl)-4-hydroxyphenyl]-methylene}-3-(3-methoxypropyl)-2-thioxo-4-thiazolidinone
5-{[3,5-bis(1,1-dimethylethyl)-4-hydroxyphenyl]-methylene}-3-[(2-ethylthio)ethyl]-4-thiazolidinone
5-{[3,5-bis(1,1-dimethylethyl)-4-hydroxyphenyl]-methyl}-3-(methylthiomethyl)-4-thiazolidinone
3-acetyl-5-{[3,5-bis(1,1-dimethylethyl)-4-hydroxyphenyl]methylene]-4-thiazolidinone
5-{[3,5-bis(1,1-dimethylethyl)-4-hydroxyphenyl]methylene}-3-[methyl(1-methylethyl)amino]-4-thiazolidinone
5-[4-hydroxybenzal]rhodanine
5-(4-hydroxy-3-methoxybenzylidene)rhodanine
5-[(4-hydroxy-3,5-dipropylphenyl)methylene]-3-[2-(dimethylamino)ethyl]-4-thiazolidinone
5-{[3,5-bis(1-methylpropyl)-4-hydroxyphenyl]-methylene}-3-methyl-4-thiazolidinone
5-{[3,5-dimethyl-4-hydroxyphenyl]methylene}-3-methyl-4-thiazolidinone
5-{[3,5-bis(1,1-dimethylethyl)-4-hydroxyphenyl]methylene}-3-(methylsulfonyl)-4-thiazolidinone
5-{[4-hydroxy-3,5-bis(1,1-dimethylethyl)phenyl]methylene}-3-(propylamino)-4-thiazolidinone
3-amino-5-{[3,5-bis(1,1-dimethylethyl)-4-hydroxyphenyl]methylene}-2-thioxo-4-thiazolidinone
5-{[3,5-bis(1-methylethyl)-4-hydroxyphenyl]methylene}-3-methyl-4-thiazolidinone
5-[(4-hydroxy-3,5-dimethoxyphenyl)methylene]3-methyl-2-thioxo-4-thiazolidinone
5-[(3,5-di-2-propenyl-4-hydroxyphenyl)methylene]-3-[2-(dimethylamino)ethyl]-4-thiazolidinone
5-[(4-hydroxy-3,5-dimethoxyphenyl)methylene]-3-methyl-2-thioxo-4-thiazolidinone Additional compounds of the present invention include 5-{[3,5-bis(1,1-dimethylethyl)-4-hydroxyphenyl]-methylene}-2-thioxo-4-thiazolidinone (referred to in the following discussion as Compound A); 5-{[3,5-bis(1,1-dimethylethyl)-4-hydroxyphenyl]methylene}-4-thiazolidinone (Compound B); 5-{[3,5-bis(1,1-dimethylethyl)-4-hydroxyphenyl]methyl}-4-thiazolidinone (Compound C); and 5-{[3,5 -bis(1,1-dimethylethyl)-4-hydroxyphenyl]methyl}-2-thioxo-4-thiazolidinone (Compound D). Compound A is taught in the art by Teuber et al., *Leibigs Ann. Chem.*, 757 (1978) (as compound V). The compound is prepared by the reaction of 3,5-di-tert-butyl-4-hydroxybenzaldehyde with rhodanine at reflux temperature in glacial acetic acid with fused sodium acetate as a catalyst. Compounds B, C, and D can be prepared from Compound A. For example, when Compound A is subjected to catalytic hydrogenation, one obtains both Compounds B and C. The relative proportions of each depends upon the temperature, pressure, and duration of hydrogenation, the solvent employed, and the particular catalyst used. For example, when Compound A is treated with 5% palladium on carbon in ethanol at 100° C. for approximately 18 hours, the relative ratios of Compound B:C are approximately 60:40. Alternatively, these transformations may be accomplished by heating Compound A in a mixture of hydrochloric acid and an alcohol such as ethanol in the presence of zinc. Reduction of the thione without affecting the benzylic double bond may be accomplished by heating the thione with a reducing agent such as tri-n-butyl tin hydride in a non-reactive solvent, such as toluene, and preferably in the presence of a free radical initiator, such as azobisisobutyronitrile. However, for such reduction to work, an N-substituted rhodanine substrate (i.e., Q cannot be —NH) must be employed.

The transformation of Compound A to D may be accomplished by a variety of methods known in the art. A preferred method is that taught by Nakamura et al., *Tetrahedron Letters*, 25, 3983 (1984). In this reaction, Compound A is treated with a dihydropyridine such as diethyl 2,6-dimethyl-1,4-dihydro-3,5-pyridine-dicarboxylate in the presence of silica gel. The reaction is best carried out in the presence of a nonreactive solvent such as benzene or toluene, preferably under an inert atmosphere. The reaction may be accomplished at temperatures from about 25° C. up to the reflux temperature of the mixture. At the preferred temperature of approximately 80° C., the reaction is essentially complete after 12–18 hours.

Other thiazolidinones may, depending on the values selected for the various substituents, be prepared in an analogous fashion. For example, compounds of formula I wherein Q is $NR^8$ and $R^8$ is hydrogen, $C_1$-$C_6$ alkyl, $C_3$-$C_8$ cycloalkyl or —$(CH_2)_n$—Y where n is as defined for formula I and Y is cyano or $NR^{11}R^{12}$ where $R^{11}$ and $R^{12}$ are each independently hydrogen or $C_1$-$C_6$ alkyl, may be prepared by the above method as taught by Teuber et al. employing the appropriate N-substituted rhodanine and $R^1$, $R^2$-substituted-4-hydroxybenzaldehyde. Alternatively, rhodanine may be used for the condensation with the aldehyde forming those species wherein Q is $NR^8$ and $R^8$ is hydrogen followed by alkylation or acylation with the appropriate $R^8$-containing halide, such as an iodide or bromide, to provide the desired N-substituted derivative of Formula I. The alkylation or acylation is usually accomplished in an inert solvent such as tetrahydrofuran (THF) or dimethylformamide (DMF) and in the presence of a strong base such as sodium hydride.

Compounds of formula I wherein Q is $NR^8$ and $R^8$ is —$(CH_2)_n$—Y (Y is $OR^9$ or $NR^{11}R^{12}$, wherein $R^9$ is hydrogen, acetyl or tosyl and $R^{11}$ and $R^{12}$ are each independently hydrogen or $C_1$-$C_6$ alkyl) may also be prepared by the following reaction scheme:

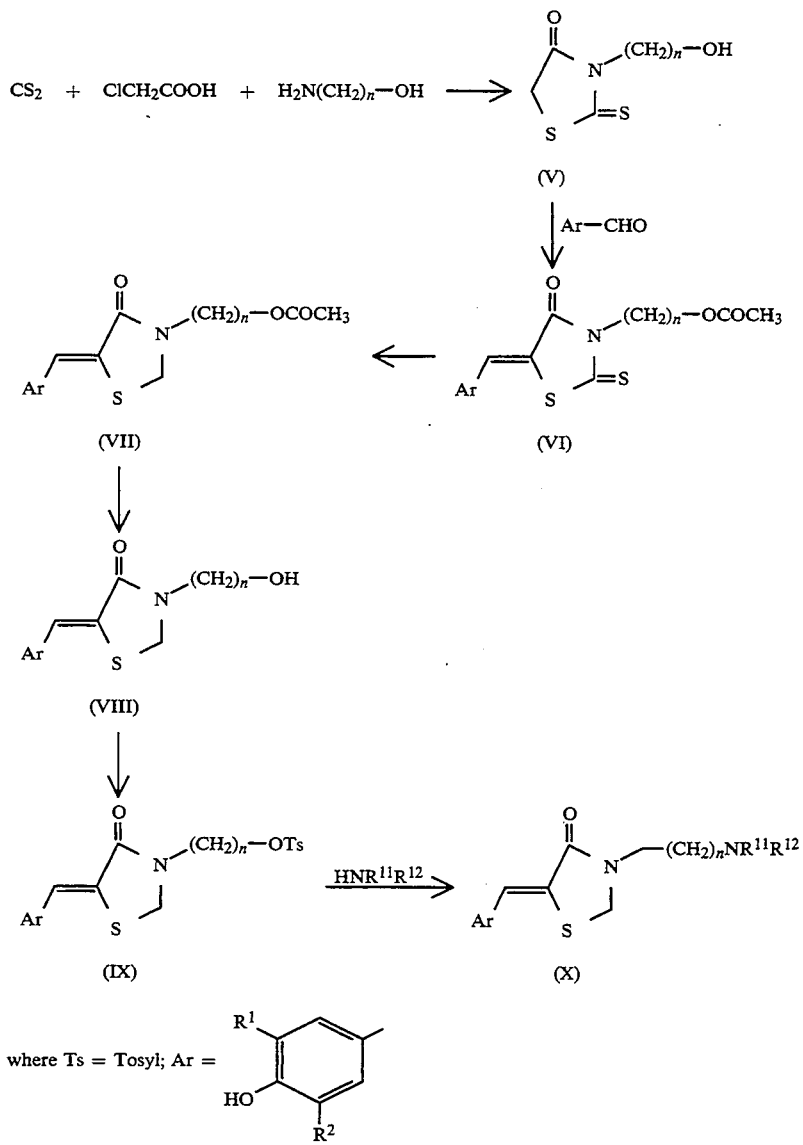

A hydroxyalkyl rhodanine V is prepared by condensing carbon disulfide, chloroacetic acid, and the appropriate hydroxyalkylamine by standard techniques. When condensed with the appropriate $R^1$,$R^2$-substituted-4-hydroxybenzaldehyde as described above, the resulting product is the condensed 2-thioxo-4-thiazolidinone VI which has been transformed into the acetyl derivative. The thioxo compound VI may optionally be converted to the methylene compound of formula VII as described above. The acetyl group of intermediate VII may be removed upon treatment with aqueous ammonia in a solvent such as acetonitrile to provide compound VIII (i.e., that compound of formula I wherein Q is $NR^8$ and $R^8$ is —$(CH_2)_n$—Y where Y is $OR^9$ and $R^9$ is hydrogen). The hydroxy compound VIII is then converted to the tosyl derivative upon treatment with p-toluenesulfonyl chloride in pyridine, preferably at temperatures of around 0° C. The versatile tosyl intermediate IX may then be transformed into additional products of the present invention upon treatment with an appropriate $HNR^{11}R^{12}$ amine, where $R^{11}$ and $R^{12}$ are as stated in the preceeding paragraph. This latter transformation is best accomplished by allowing IX to react in the presence of a molar excess of the amine. Once again, a solvent such as acetonitrile is useful for accomplishing this transformation.

The corresponding 1,3-oxothiolan-5-ones may be prepared from $\beta$-(3,5-di-t-butyl-4-hydroxyphenyl)-$\alpha$-mercaptoacrylic acid (XI). Compound XI may be treated with carbon disulfide to prepare the thione analog (formula I, Q=—O—, $R^6$ and $R^7$ are=S), while reaction of XI with formic acid provides the corresponding desthione (formula I, Q=—O—, $R^6$ and $R^7$ are each hydrogen). Compound XI can be prepared by known methods (see, e.g., Campaigne et al., *J. Org. Chem.*, 26, 359 (1961); id., 26, 1326 (1961); Chakrabarti, et al, *Tetrahedron*, 25 (14), 2781 (1969)), or upon heating Compound A with dilute aqueous base (See Example 17A).

Compounds of the present invention wherein Q is $NR^8$ and $R^8$ is —$(CH_2)_n$—Y (n=0) and Y is $NR^{11}R^{12}$ and $R^{11}$ and $R^{12}$ are as defined for formula I may be prepared according to the following reaction sequence:

amine and acetonitrile to render intermediate XIII. XIII is then treated with hydrazine to render the $R^{11}$,$R^{12}$-hydrazine, XIV. XIV may alternatively be prepared by the reduction of a nitroso-$R^{11}R^{12}$ amine using zinc dust and acetic acid or aluminum and a strong base. The nitroso-$R^{11}R^{12}$ amine itself is prepared from an $R^{11}$,$R^{12}$ amine as described in *J. Am. Chem. Soc.* 77, 790 (1955) by treatment with sodium nitrite in HCl. The resultant $R^{11}$, $R^{12}$-hydrazine (XIV) is then treated with carbon disulfide, chloroacetic acid and triethylamine to yield intermediate XV. Condensation of said intermediate XV with the appropriate $R^1$,$R^2$-substituted-4-hydroxybenzaldehyde (i.e., ArCHO) renders XVI. As described previously, the thione may be reduced by treatment with a reducing agent such as tri-n-butyltin hydride in a non-reactive solvent such as toluene, preferably in the presence of a free radical initiator such as azobisisobutyronitrile. Preparation of the species wherein one of $R^{11}$ or $R^{12}$ is hydrogen may be effected before or after reduction of the thione as desired by heating the disubstituted compound in a mixture of ethanol/water in the presence of a catalyst such as a rhodium catalyst.

Those compounds where X is

and m is 1 or 2 are readily prepared from the sulfide (i.e., m=0) as by treatment with an oxidizing agent, such as m-chloroperbenzoic acid, in an appropriate

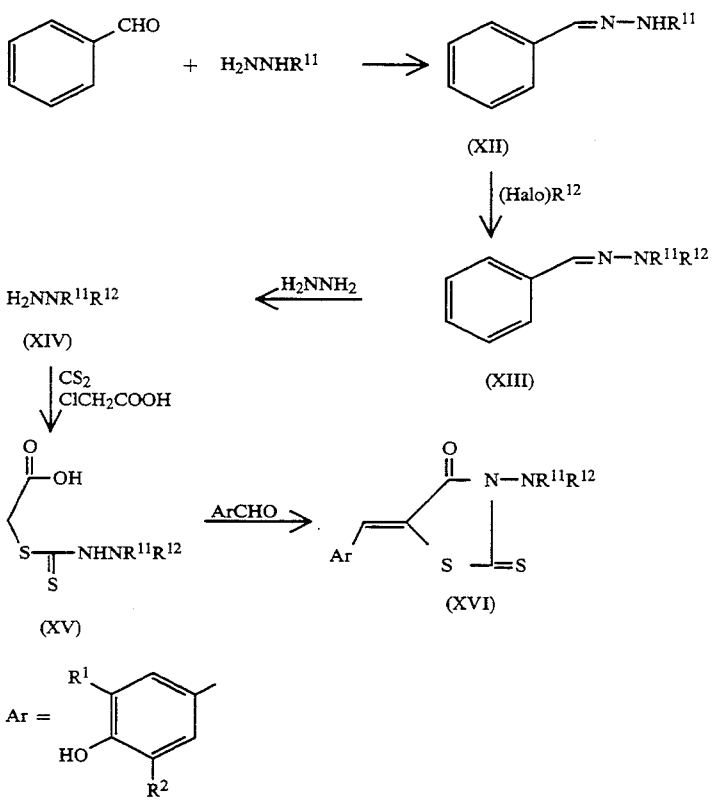

The $R^{11}$-substituted hydrazine is treated with benzaldehyde in an alcoholic (preferably methanol) solvent to yield intermediate XII which, in turn, is reacted with the appropriate $R^{12}$-halide in the presence of triethylorganic solvent, such as chloroform, for a time sufficient to effect the desired oxidation.

Compounds wherein $R^3$ is $C_1$-$C_6$ alkyl are prepared by conventional Friedel-Crafts alkylation of the appropriate $R^1$, $R^2$-substituted phenol, followed by condensation with rhodanine, or the desired N-substituted rhodanine, as described herein or is used as described in other reaction schemes depicted herein.

It will be readily appreciated by one skilled in the art that the aryl portion of the present compounds are either commercially available or may be readily prepared by known techniques from commercially available starting materials. For example, p-hydroxybenzaldehyde may be alkylated under Friedel-Crafts conditions to yield an alkylbenzaldehyde which in turn may itself be alkylated. Similarly, the rhodanine or N-substituted rhodanine starting material is either commercially available or may be prepared by well known methodology from commercially available starting materials.

Further, the skilled artisan will readily appreciate that the pyrrolidones described for formula III (i.e., $X^b$=—$CH_2$—) which are useful in a treatment method for preventing ischemia-induced cell damage, are prepared in analogous fashion to that described herein for the thiazolidinones. That is to say, the pyrrolidones are conveniently prepared by the condensation of an appropriately substituted 2-pyrrolidone with the desired $R^1$,$R^2$-substituted aryl moiety as described, for example, by Katsumi et al., *Chem. Pharm. Bull.* 34 (4), 1619 (1986).

Those compounds of formula I wherein one of $R^6$ or $R^7$ is hydrogen and the other is —OH are conveniently prepared from their respective precursors (i.e., those compounds of formula I where $R^6$ and $R^7$ are both hydrogen and $R^1$, $R^2$, $R^3$, $R^4$ $R^5$, X and Q are as defined in formula I) by the treatment of the precursor with, for example, trifluoroacetic anhydride in an inert solvent (preferably methylene chloride) at reduced temperatures. Similarly, compounds of formula I where, in the definition of Q, Y is cyano are prepared by treating the non-cyanated compounds of the present invention with the desired halo-substituted aliphatic nitrile. From the cyano derivative the tetrazolyl is prepared as by treatment with tri-N-butyl tin azide in, for example, ethylene glycol dimethyl ether. Other compounds of formula I may be prepared as more fully described below from compounds whose synthesis was described generically, supra.

Depending upon the definitions of $R^3$, $R^4$ and $R^5$, the compounds of formula I may exist in various isomeric forms. This invention is not related to any particular isomer but includes all possible individual isomers and racemates.

The following examples further illustrate the preparation of the compounds of this invention. The examples are illustrative only and are not intended to limit the scope of the invention in any way.

EXAMPLE 1

5-{[3,5-bis(1,1-dimethylethyl)-4-hydroxyphenyl]methylene}-2-thioxo-4-thiazolidinone (Compound A)

Under a nitrogen atmosphere, 117.2 g of 3,5-di-tert-butyl-4-hydroxybenzaldehyde, 66.6 g of rhodanine, and 143.5 g of fused sodium acetate were heated at reflux in 2500 ml of glacial acetic acid. After heating for 23 hours, the reaction mixture was cooled and poured into a mixture of 1 liter of ethanol and 1 liter of ice with stirring. 500 ml of water were added and, after stirring for 30 minutes, the resulting precipitate was recovered by filtration. The solid was slurried with 500 ml of ethyl acetate and filtered. The precipitate was then dissolved in 3 liters of ethanol, heated to boiling, and water was added until the solution remained cloudy, approximately 450 ml. Upon cooling to room temperature, 99.6 g of the desired title product were recovered by filtration, m.p. approximately 260° C.

Analysis for $C_{18}H_{23}NO_2S_2$: Calculated: C, 61.86; H, 6.63; N, 4.01; Found: C, 62.13; H, 6.55; N, 4.15.

EXAMPLES 2-3

5-{[3,5-bis(1,1-dimethylethyl)-4-hydroxyphenyl]methylene}-4-thiazolidinone (Compound B) and 5-{[3,5-bis(1,1-dimethylethyl)-4-hydroxyphenyl]methyl}-4-thiazolidinone (Compound C)

A solution of 69.90 g of 5-{[3,5-bis(1,1-dimethylethyl)-4-hydroxyphenyl]methylene}-2-thioxo-4-thiazolidinone in 4 liters of ethanol was hydrogenated at 500 pounds per square inch (psi) in the presence of 200 g of 5% palladium on carbon overnight at 100° C. The reaction mixture was filtered and evaporated to dryness. In sections, the material was dissolved in 1 volume of hot ethyl acetate, diluted with 2 volumes of hexane, filtered, and loaded onto a silica gel chromatography column. Elution with 35% ethyl acetate in hexane provided various fractions which were combined according to the purities of the respective compounds. A total of 4.6 g of Compound B were isolated by chromatography. Fractions which were predominantly Compound B were crystallized from ethyl acetate/hexane providing a total yield of Compound B of 13.79 g. Rechromatography of fractions containing impure Compound C on silica eluting with 25% ethyl acetate in hexane provided 9.82 g of Compound C.

2. 5-{[3,5-bis(1,1-dimethylethyl)-4-hydroxyphenyl]methylene}-4-thiazolidinone, m.p. 209°–213° C.

Analysis for $C_{18}H_{25}NO_2S$: Calculated: C, 67.67; H, 7.89; N, 4.38; Found: C, 67.44; H, 8.11; N, 4.65.

3. 5-{[3,5-bis(1,1-dimethylethyl)-4-hydroxyphenyl]methyl}-4-thiazolidinone, m.p. 149°–152° C.

Analysis for $C_{18}H_{27}NO_2S$: Calculated: C, 67.25; H, 8.47; N, 4.36; Found: C, 67.43; H, 8.44; N, 4.21.

EXAMPLE 4

5-{[3,5-bis(1,1-dimethylethyl)-4-hydroxyphenyl]methylene}-4-oxo-3-thiazolidinecarboxylic acid, methyl ester Under a nitrogen atmosphere, 7.03 g of the compound of Example 2 was dissolved in 330 ml of THF to which was added 581 mg of sodium hydride. The mixture was stirred for 10 minutes after which about 2 g of methyl chloroformate was added and the resulting mixture was stirred for an additional 50 minutes. Water (500 ml) and 7 ml of 1N hydrochloric acid (pH of solution about 3) were added. The resultant mixture was extracted twice with 200 ml portions of ethyl acetate. The organic extracts were combined, stripped to dryness, and crystallized from 15 ml of ethylacetate and 25 ml hexane to render the title compound, m.p. 165°–167.5° C.

Analysis for $C_{20}H_{27}NO_4S$: Calculated: C, 63.63; H, 7.21; N, 3.71; Found: C, 63.76; H, 7.33; N, 3.68.

EXAMPLE 5

5-{[3,5-bis (1,1-dimethylethyl)-4-hydroxyphenyl]methylene}-4-oxo-3-thiazolidineacetamide Under a nitrogen atmosphere, 7.03 g of the compound of Example 2 was dissolved in 330 ml of THF. To this was added 0.581 g of sodium hydride and the mixture was stirred for 10 minutes. Iodoacetamide 4.07 g) was added and the resultant mixture was heated at reflux temperature for one hour and then cooled. The solution was then poured into 500 ml of a mixture of rapidly stirred ice/water. The pH of the mixture was reduced to about pH 3 by the addition of 10 ml of 1N hydrochloric acid. The resultant mixture was extracted with three 200 ml portions of ethyl acetate. The extracts were combined, stripped, and crystallized from a mixture of 120 ml of ethyl acetate and 100 ml hexane to render 2.79 g of the title compound, m.p. 232–235.

Analysis for $C_{20}H_{28}N_2O_3S$: Calculated: C, 63.80; H, 7.50; N, 7.44; Found: C, 63.53; H, 7.67; N, 7.14.

EXAMPLE 6

5-{[3,5-bis(1,1-dimethylethyl)-4-hydroxyphenyl]methylene}-3-[2-(methylthio)ethyl]-4-thiazolidinone 26.7 g of 5-{[3,5-Bis(1,1-dimethylethyl)-4-hydroxyphenyl]methylene}-4-thiazolidinone (i.e., the compound of Example 2) was dissolved in 418 ml of DMF to which was added 3.34 g of a 60% sodium hydride dispersion. The resultant mixture was stirred at 100° C. under an argon atmosphere. To this was added 8.33 ml of methylthioethyl chloride and the resulting black solution was stirred at 100° C. for 6 days. The material was allowed to cool to 30° C. after which insoluble material was filtered off. The solid was washed with DMF until its color was gone leaving a white solid which was discarded. The pH of the filtrate and washings was adjusted to 1.5 by the addition of 1N hydrochloric acid with stirring. The mixture was then diluted with a mixture of 1000 ml of diethyl ether and 500 ml of 1N hydrochloric acid which was then shaken and separated. The organic layer was washed with two portions of water and one portion of brine and subsequently dried over sodium sulfate, filtered, evaporated and chased with chloroform to give a black foam/oil. This material was triturated with about 75 ml of chloroform and then filtered and the insoluble solid was washed with additional chloroform until its brown color was gone. The filtrate was then loaded onto a silica gel column which was eluted with 8000 ml of a gradient of 10–30% ethyl acetate in hexane. The various fractions containing the desired product were combined and again loaded onto a silica gel column and eluted with 8000 ml of a gradient of 10–35% acetone in hexane. The fractions containing the desired product were recrystalled with hexane/ethyl acetate to give 1.2 g of the title compound as a tan/orange solid, m.p. 165.5°–168° C.

Analysis for $C_{21}H_{31}NO_2S_2$: Calculated: C, 64.08; H, 7.94; N, 3.56; Found: C, 63.99; H, 8.13; N, 3.45.

EXAMPLE 7

5-{[3,5-bis (1,1-dimethylethyl)-4-hydroxyphenyl]methylene}-3-(2-methoxyethyl)-4-thiazolidinone Under an argon atmosphere, 9.58 g of the compound of Example 2 was dissolved in THF with stirring. To this was added 1.2 g of a 60% sodium hydride dispersion and the reaction mixture was then heated to reflux. 2.82 ml of methoxyethylbromide were then added and the resultant mixture was allowed to stir at reflux for five days. After five days, 0.2 equivalents of potassium iodide were added and the reaction was allowed to continue at reflux temperature for an additional two days. The mixture was then allowed to cool and was diluted with diethyl ether and water. The pH of the mixture was adjusted to pH 2 by the addition of 1N hydrochloric acid with stirring. Organic and aqueous layers formed and were separated and the organic layer was washed with saturated sodium bicarbonate, then brine, and subsequently dried over sodium sulfate, filtered, evaporated and then chased with chloroform. The resultant material was then dissolved in 50 ml of chloroform and a precipitate formed. An additional 25 ml of chloroform was added and the mixture was heated. The resultant solution was filtered, chromatographed on silica gel, and subsequently eluted with 8000 ml of a 10–30% gradient of ethyl acetate in hexane followed by elution with 4000 ml of a 30–40% gradient of ethyl acetate in hexane. The various fractions containing the desired product were combined, evaporated to dryness and then chased with chloroform to render an orange sticky solid. This material was then dissolved in 15 ml of ethyl acetate with heating on a steam bath and subsequently diluted with 250 ml of hexane. The mixture was allowed to cool to room temperature, with precipitate forming, and allowed to stand for three days. The material was filtered and washed with hexane to yield 5.16 g of the title compound, m.p. 147°–149° C.

Analysis for $C_{21}H_{31}NO_3S$: Calculated: C, 66.80; H, 8.28; N, 3.71; Found: C, 67.04; H, 8.30; N, 3.74.

EXAMPLE 8

5-{[3,5-bis(1,1-dimethylethyl)-4-hydroxyphenyl]methyl}-2-thioxo-4-thiazolidinone (Compound D)

Under a nitrogen atmosphere, 13.98 g of 5-{[3,5-bis(1,1-dimethylethyl)-4-hydroxyphenyl]methylene}-2-thioxo-4-thiazolidinone, 13.17 g of diethyl 2,6-dimethyl-1,4-dihydro-3,5-pyridinedicarboxylate and 600 ml of toluene were stirred to effect solution. Forty grams of silica gel 60 (finer than 230 mesh) previously dried in vacuo at 50° C. for 7 hours were added to the reaction. The reaction was heated at reflux for 18 hours and filtered hot. The filtrate was evaporated to dryness. The residue was dissolved in 500 ml of ethyl acetate, washed 5 times each with 400 ml of 1N hydrochloric acid, dried over sodium sulfate, filtered, and evaporated in vacuo to provide a yellow solid. Chromatography over silica gel eluting with 2.5% ethyl acetate in toluene provided 8.0 g of the desired title product, m.p. 178°–179° C.

Analysis for $C_{18}H_{25}NO_2S_2$: Calculated: C, 61.50; H, 7.17; N, 3.98; Found: C, 61.28; H, 7.19; N, 3.94.

EXAMPLE 9

5-{[3,5-bis(1,1-dimethylethyl)-4-hydroxyphenyl]methylene}-3-methyl-2-thioxo-4-thiazolidinone The title compound was prepared in 76% yield from 3,5-di-tert-butyl-4-hydroxybenzaldehyde and N-methylrhodanine following the procedure of Example 1, m.p. >230° C.

Analysis for $C_{19}H_{25}NO_2S_2$: Calculated: C, 62.77; H, 6.93; N, 3.85; S, 17.64; Found: C, 62.54; H, 7.05; N, 3.66; S, 17.82.

EXAMPLE 10

5-{[3,5-bis(1,1-dimethylethyl)-4-hydroxyphenyl]methylene}-3-methyl-4-thiazolidinone The title compound was prepared in 71% yield from 10.31 g of the thione of Example 9 upon heating with 38.15 ml of tri-n-butyl tin hydride and 1.16 g of azobisisobutyronitrile (AIBN) in 142 ml of toluene at reflux temperature for one hour. The product was isolated by adding water to the cooled reaction mixture, separating the layers, washing the organic layer with 1N hydrochloric acid and a saturated sodium chloride solution, drying over magnesium sulfate, concentrating in vacuo, and purifying the residue by chromatography over silica gel eluting with a 10–50% hexane in ethyl acetate gradient. The purified product had a melting point of 142°–144° C.

Analysis for $C_{19}H_{27}NO_2S$: Calculated: C, 68.43; H, 8.16; N, 4.20; Found: C, 68.68; H, 8.00; N, 3.97.

EXAMPLE 11

5-{[3,5-bis(1,1-dimethylethyl)-4-hydroxyphenyl]methyl}-3-methyl-4-thiazolidinone To 100 ml of THF was added 6.43 g of the compound of Example 3. Sodium hydride (0.9 g) was added, resulting in the evolution of a gas. 1.25 ml (1.0 eq.) of iodomethane was added and the resultant mixture was stirred at room temperature for 23 hours after which the mixture was diluted with a volume of diethyl ether and 1N HCl. The organic layer was separated and dried over sodium sulfate, filtered and evaporated. The resultant solid was chased with chloroform to render an orange foam. A 5.93 g sample of this material was dissolved in 14 ml of a hot mixture of ethyl acetate diluted with 225 ml of hexane and then allowed to cool to room temperature overnight. The solvent was evaporated and the resultant solid was dissolved in 40 ml of a hot mixture of diethyl ether diluted with about 400 ml of hexane. The mixture was allowed to cool to room temperature overnight and a precipitate formed which was collected by filtration, washed with hexane and dried in vacuo to render 3.98 g of the desired, title compound, m.p. 102°–105° C.

Analysis for $C_{19}H_{29}NO_2S$: Calculated: C, 68.02; H, 8.71; N, 4.17; Found: C, 68.22; H, 8.80; N, 4.21.

EXAMPLE 12

5-{[3,5-bis (1,1-dimethylethyl)-4-hydroxyphenyl]methylene}-3-methyl-4-thiazolidinone, 1-oxide Under a nitrogen atmosphere, 6.67 g of the compound of Example 10 was dissolved in 100 ml of chloroform with stirring and the resultant mixture was cooled to 4° C. Meta-chloroperbenzoic acid was added dropwise (with additional chloroform) after which the reaction mixture was poured into a separatory funnel and washed with saturated sodium bicarbonate. The layers were separated, and the organic layer was dried over sodium sulfate, filtered and evaporated to give a white foam. The foam was dissolved in 70 ml of ethyl acetate with heating on a steam bath and diluted with 125 ml of hexane while boiling. A precipitate formed and the reaction mixture was allowed to cool to room temperature overnight. The precipitate was filtered, subsequently washed with hexane, and dried under vacuum at room temperature for two hours to render 6.10 g of the title compound, m.p. 183°–184° C.

Analysis for $C_{19}H_{27}NO_3S$: Calculated: C, 65.30; H, 7.79; N, 4.01; Found: C, 65.46; H, 7.68; N, 4.01.

EXAMPLE 13

5-{[3,5-bis(1,1-dimethylethyl)-4-hydroxyphenyl]methylene}-3-methyl-4-thiazolidinone, 1,1-dioxide Under a nitrogen atmosphere, 1 g of the compound of Example 10 was dissolved in 15 ml of chloroform with stirring while cooled in an ice bath. To this was added, dropwise, 1.29 g of m-chloroperbenzoic acid and an additional 18 ml of chloroform such that the addition was complete in 15 minutes. The mixture was removed from the ice bath, stirred at room temperature for 22 hours, transferred to a separatory funnel and then washed with a saturated sodium bicarbonate solution. The layers were separated and the organic layer was washed with brine, separated, dried over sodium sulfate, filtered and evaporated. The resultant residue was taken up in 12 ml of ethyl acetate and diluted with 50 ml hexane while boiling on a steam bath. The mixture was allowed to cool to room temperature overnight and the resultant precipitate was filtered, washed with hexane and dried in vacuo to yield 0.75 g of the desired titled compound, m.p. 217°–221° C.

Analysis for $C_{19}H_{27}NO_4S$: Calculated: C, 62.44; H, 7.45; N, 3.83; Found: C, 62.17; H, 7.26; N, 3.95.

EXAMPLE 14

5-{[3,5-Bis(1,1-dimethylethyl)-4-hydroxyphenyl]methylene}-3-ethyl-4-thiazolidinone To a solution of 9.58 g of 5-{[3,5-bis(1,1-dimethylethyl)-4-hydroxyphenyl]methylene}-4-thiazolidinone in 150 ml of tetrahydrofuran were added 1.20 g of a 60% dispersion of sodium hydride in mineral oil. After gas evolution ceased, 2.4 ml of ethyl iodide were added and the reaction mixture was stirred for two days under an argon atmosphere. The mixture was heated at reflux for six hours, cooled, diluted with diethyl ether and water, and adjusted to pH 3 with 1N hydrochloric acid. The layers were separated, and the organic layer was washed with a saturated sodium bicarbonate solution followed by a saturated sodium chloride solution. Concentration of the dried organic solution and chromatography of the resulting residue over silica gel eluting with a 10–30% ethyl acetate in hexane gradient provided 3.65 g of the desired title product, m.p. 169°–172.5° C.

Analysis for $C_{20}H_{29}NO_2S$: Calculated: C, 69.12; H, 8.41; N, 4.03; Found: C, 69.39; H, 8.52; N, 4.30.

EXAMPLES 15–16

The following compounds were prepared from the appropriate alkyl iodide according to the procedure of Example 14.

15. 5-{[3,5-bis(1,1-dimethylethyl)-4-hydroxyphenyl]methylene}-3-propyl-4-thiazolidinone, 60% yield, m.p. 145°–146.5° C.

Analysis for $C_{21}H_{31}NO_2S$: Calculated: C, 69.76; H, 8.64; N, 3.87; Found: C, 70.05; H, 8.76; N, 4.01.

16. 5-{[3,5-bis(1,1-dimethylethyl)-4-hydroxyphenyl]methylene}-3-butyl-4-thiazolidinone, 60% yield, m.p. 168.5°–169.5° C.

Analysis for $C_{22}H_{33}NO_2S$: Calculated: C, 70.36; H, 8.86; N, 3.73; Found: C, 70.60; H, 8.81; N, 3.97.

EXAMPLE 17

4-{[3,5-bis(1,1-dimethylethyl)-4-hydroxyphenyl]methylene}-1,3-oxothiolan-5-one

A. Preparation of β-(3,5-di-t-butyl-4-hydroxyphenyl)-α-mercaptoacrylic acid

A solution of 174.5 g of 5-{[3,5-bis(1,1-dimethylethyl)-4-hydroxyphenyl]methylene}-2-thioxo-4-thiazolidinone in 1250 ml of a 10% sodium hydroxide solution was heated on a steam bath for four hours. Decolorizing carbon was added and the mixture filtered through a high flow diatomaceous earth pad. The filtrate was chilled by adding ice and treated with 6N hydrochloric acid. The precipitated product was recovered by filtration, washed with water, and dried providing 150 g of the desired subtitled intermediate.

B. Preparation of 4-{[3,5-bis(1,1-dimethylethyl)-4-hydroxyphenyl]methylene}-1,3-oxothiolan-5-one Following the procedure of *Agr. Biol. Chem.*, 29(8), 728 (1965), six grams of the mercaptoacrylic acid from above were heated on a steam bath with 36 ml of acetic acid and 6 ml of formaldehyde (37% solution) for one hour. Evaporation of the mixture and chromatography of the residue over silica gel provided 1.7 g of the desired product, m.p. 127°–129° C.

Analysis for $C_{18}H_{24}O_3S$: Calculated: C, 67.47; H, 7.55; Found: C, 67.71; H, 7.62.

EXAMPLES 18–19

The following compounds were prepared according to the procedure of Example 1 employing the appropriate N-substituted rhodanine.

18. 5-{[3,5-bis(1,1-dimethylethyl)-4-hydroxyphenyl]methylene}-3-cyclopropyl-2-thioxo-4-thiazolidinone, 93% yield, m.p. 158°–168° C.

19. 5-{[3,5-bis(1,1-dimethylethyl)-4-hydroxyphenyl]methylene}-3-dimethylamino-2-thioxo-4-thiazolidinone, 65% yield.

EXAMPLES 20–21

The thiones of Examples 18–19 were reduced using the procedure of Example 10 to provide the following compounds of the invention.

20. 5-{[3,5-bis(1,1-dimethylethyl)-4-hydroxyphenyl]methylene}-3-cyclopropyl-4-thiazolidinone, 46% yield, m.p. 162°–164° C.

Analysis for $C_{21}H_{29}NO_2S$: Calculated: C, 70.16; H, 8.13; N, 3.90; Found: C, 69.91; H, 8.23; N, 3.75.

21. 5-{[3,5-bis(1,1-dimethylethyl)-4-hydroxyphenyl]methylene}-3-dimethylamino-4-thiazolidinone, 41% yield, m.p. 138°–141° C.

Analysis for $C_{20}H_{30}N_2O_2S$: Calculated: C, 66.26; H, 8.34; N, 7.73; Found: C, 66.55; H, 8.59; N, 7.47.

EXAMPLE 22

5-{[3,5-bis(1,1-dimethylethyl)-4-hydroxyphenyl]methylene}-3-(dimethylamino)-4-thiazolidinone, 1-oxide Under a nitrogen atmosphere, 9.06 g of the compound of Example 21 was dissolved in 125 ml of chloroform with stirring while cooled in an ice bath. To this was added (dropwise) 5.39 g of meta-chloroperbenzoic acid in 75 ml of chloroform over a period of 25 minutes at 0° C. After an additional 10 minutes, the reaction mixture was transferred to a separatory funnel, washed with saturated sodium bicarbonate and the layers separated. The aqueous layer was washed with chloroform. This wash was added to the original chloroform extract resulting in a slow breaking emulsion. The organic layer was dried over sodium sulfate, filtered, washed and the solvent removed by evaporation. The resultant residue was subsequently taken up in about 225 ml of ethyl acetate with heating on a steam bath and then diluted with about 100 ml of hexane. A precipitate formed and the resultant mixture was allowed to cool to room temperature overnight. The precipitate was filtered, washed with hexane, allowed to air dry for one hour and subsequently dissolved in 100 ml of isopropyl alcohol on a steam bath. The resultant solution was allowed to cool to room temperature overnight resulting in a precipitate which was again washed with hexane and dried under vacuum at 80° C. for about four hours to yield 5.41 g of the title compound, m.p. 198°–201° C.

Analysis for $C_{20}H_{30}N_2O_3S$: Calculated: C, 63.46; H, 7.97; N, 7.40; Found: C, 63.68; H, 7.78; N, 7.56.

EXAMPLE 23

5-{[3,5-bis(1,1-dimethylethyl)-4-hydroxyphenyl]methylene}-4-thiazolidinone, 1-oxide Utilizing the procedures set forth in Example 22, 5.12 g of the title compound was prepared from 5-[[3,5-bis(1,1-dimethylethyl)-4-hydroxyphenyl]methylene]-3-dimethylamino-4-thiazolidinone (i.e., the compound of Example 21), m.p. 103°–110° C.

Analysis for $C_{18}H_{25}NO_3S$: Calculated: C, 63.77; H, 8.41; N, 3.54; Found: C, 64.11; H, 8.26; N, 3.55.

Utilizing the procedures set forth herein the following additional compounds were prepared.

EXAMPLE 24

5-{[3,5-bis(1,1-dimethylethyl)-4-hydroxyphenyl]methylene}-3-(2-propenyl)-4-thiazolidinone, m.p. 154.5°–156.5° C.

Analysis for $C_{21}H_{29}NO_2S$: Calculated: C, 70.16; H, 8.13; N, 3.90; S, 8.92; Found: C, 70.27; H, 8.21; N, 4.01; S, 9.09.

EXAMPLE 25

5-{[3,5-bis(1,1-dimethylethyl)-4-hydroxyphenyl]methylmethylene}-3-methyl-4-thiazolidinone, m.p., 152.5°–153.5° C.

Analysis for $C_{20}H_{29}NO_2S$: Calculated: C, 69.12; H, 8.41; N, 4.03; Found: C, 69.18; H, 8.25; N, 4.26.

EXAMPLE 26

5-{[3,5-bis(1,1-dimethylethyl)-4-hydroxyphenyl]methylene}-3-[2-(acetyloxy)ethyl]-4-thiazolidinone

A. Preparation of N-(2-hydroxyethyl)rhodanine

Sixty milliliters of carbon disulfide were added to 200 ml of diethyl ether. The solution was chilled to −5° C. and slowly added to a solution of 138 ml of ethanolamine in 250 ml of ethanol. After holding the mixture at ambient temperature for 16 hours, the resulting top layer was decanted and the residual oil washed twice with 50 ml of diethyl ether. To the oil was added a solution of 71 g of chloroacetic acid in 150 ml of 5N sodium hydroxide at 0° C. The cooling bath was removed and the reaction was allowed to stand for 75 minutes. The mixture was poured into 400 ml of 6N hydrochloric acid and the resulting mixture heated to 91° C. for 20 minutes. The heat was removed, and the solution allowed to stand for 5 hours at ambient temperature. An oily organic layer was separated from the aqueous layer and the aqueous layer extracted twice with 250 ml of ethyl acetate. The organic layers were combined, washed twice with a saturated sodium chloride solution, dried and concentrated in vacuo to provide 113.4 g of the desired subtitled intermediate, which was used without further purification.

B. Preparation of
5-{[3,5-bis(1,1-dimethylethyl)-4-hydroxyphenyl]methylene}-3-[2-(acetyloxy)ethyl]-2-thioxo-4-thiazolidinone A mixture of 124 g of 3,5-di-tert-butyl-4-hydroxybenzaldehyde, 103.1 g of the subtitle intermediate of Example 26A above, 346.9 g of sodium acetate, and 2.65 l of glacial acetic acid was heated at reflux temperature for 7.5 hours under a nitrogen atmosphere. The heat was removed and the mixture allowed to cool overnight with stirring. The resulting precipitate was removed by filtration and the filtrate concentrated in vacuo. Two liters of ethyl acetate were added to the residue followed by 1.5 l of water. The layers were separated and the water layer extracted with 500 ml of ethyl acetate. The organic layers were combined, washed with water and a sodium bicarbonate solution, dried over sodium sulfate, and concentrated in vacuo. The residue was purified by chromatography over silica gel, eluting with a gradient of toluene to 7% ethyl acetate in toluene. The appropriate fractions were combined and concentrated in vacuo. The residue was crystallized from 75 ml of ethanol to provide 10.28 g of the desired subtitled intermediate, m.p. 140°-143° C.

C.
5-{[3,5-bis(1,1-dimethylethyl)-4-hydroxyphenyl]methylene}-3-[2-(acetyloxy)ethyl]-4-thiazolidinone Under a nitrogen atmosphere, 82.2 g of 5-{[3,5-bis(1,1-dimethylethyl)-4-hydroxyphenyl]methylene}-3-[2-(acetyloxy)ethyl]-2-thioxo-4-thiazolidinone in 950 ml of toluene was heated to 65° C. Tri-n-butyl tin hydride (219.7 g) and AIBN (4.65 g) were added and the solution heated at reflux temperature for an additional 10 minutes. After cooling, the mixture was washed with 1.25 l of 1N hydrochloric acid followed by 500 ml of a saturated sodium chloride solution. The organic layer was stripped and allowed to stand overnight, during which time a precipitate separated. The liquid portion was decanted off, and the resulting residue was purified by chromatography over silica gel, eluting with a gradient of 25–50% of ethyl acetate in hexane. The appropriate fractions were combined and concentrated in vacuo to provide 45.7 g of the desired titled compound, m.p.=152°-155° C.

Analysis for $C_{22}H_{31}NO_4S$: Calculated: C, 60.66; H, 6.71; N, 3.22; Found: C, 60.71; H, 6.90; N, 3.21.

EXAMPLE 27

5-{[3,5-bis(1,1-dimethylethyl)-4-hydroxyphenyl]methylene}-3-(2-aminoethyl)-4-thiazolidinone A. Preparation of
5-{[3,5-bis(1,1-dimethylethyl)-4-hydroxyphenyl]methylene}-3-(2-hydroxyethyl)-4-thiazolidinone A solution of 85.2 g of 5-{[3,5-bis(1,1-dimethylethyl)-4-hydroxyphenyl]methylene}-3-{2-(acetyloxy)ethyl]-4-thiazolidinone from Example 26 in 1.5 l of acetonitrile was treated with 1 l of concentrated ammonium hydroxide. The reaction mixture was allowed to stand for approximately 90 hours at room temperature. The solution was concentrated in vacuo and 500 ml of ethyl acetate were added, with the pH adjusted to 3.0 with concentrated hydrochloric acid. The layers were separated and the aqueous layer extracted with 250 ml of ethyl acetate. The combined organic layers were washed with 250 ml of a saturated sodium chloride solution and concentrated in vacuo. The residue was crystallized from 95 ml of hexane and 70 ml of ethyl acetate to provide 35.68 g of the desired subtitled intermediate, m.p. 131°-135° C.

Analysis for $C_{20}H_{29}NO_3S$: Calculated: C, 66.08; H, 8.04; N, 3.85; Found: C, 65.91; H, 8.21; N, 3.96.

B. Preparation of
5-{[3,5-bis(1,1-dimethylethyl)-4-hydroxyphenyl]methylene}-3-[2-(tosyloxy)ethyl]-4-thiazolidinone A solution of 30.2 g of the hydroxyethyl intermediate of Example 27A, above, in 415 ml of pyridine was cooled to −3° C. and 39.6 g of p-toluenesulfonyl chloride was added with stirring. After stirring the mixture at 0° C. for 4 hours, the solution was stored in a refrigerator overnight at −10° C. Approximately 1 l of ice water was added and the mixture extracted twice with 700 ml of diethyl ether. The combined organic layers were washed twice with 1 l of 1N hydrochloric acid and ice, dried over sodium sulfate and concentrated in vacuo to provide 41.7 g of the desired tosyl intermediate, which was used without further purification.

C. Preparation of
5-{[3,5-bis(1,1-dimethylethyl)-4-hydroxyphenyl]methylene}-3-(2-aminoethyl)-4-thiazolidinone A mixture of 13 g of the tosyl intermediate of Example 27B, above, 250 ml of concentrated ammonium hydroxide, and 250 ml of acetonitrile was stirred for 2 days at room temperature. The mixture was concentrated in vacuo and diluted with 500 ml of ethyl acetate. The pH was adjusted to 9.0 and the layers separated. The organic layer was washed twice with water, dried, and concentrated in vacuo. The residue was purified by chromatography over silica gel, eluting with a gradient from methylene chloride to 90:10:1 methylene chloride/ethanol/ammonium hydroxide, respectively. The desired fractions were combined and concentrated in vacuo. The residue was triturated with hexane to provide 1.47 g of the desired title product, m.p. 176°-178° C.

Analysis for $C_{20}H_{30}N_2O_2S$: Calculated: C, 66.26; H, 8.32; N, 7.73; Found: C, 66.25; H, 8.24; N, 7.59.

EXAMPLES 28-30

The following compounds were prepared by reacting the intermediate of Example 27B with the appropriate amine according to the procedures described herein.

28. 5-{[3,5-bis(1,1-dimethylethyl)-4-hydroxyphenyl]methylene}-3-[2-(methylamino)ethyl]-4-thiazolidinone, 28% yield, m.p. 137°-140° C.

Analysis for $C_{21}H_{32}N_2O_2S$: Calculated: C, 66.98; H, 8.57; N, 7.44; Found: C, 66.76; H, 8.33; N, 7.24.

29. 5-{[3,5-bis(1,1-dimethylethyl)-4-hydroxyphenyl]methylene}-3-[2-(dimethylamino)ethyl]-4-thiazolidinone, 64% yield, m.p. 148°-153° C.

Analysis for $C_{22}H_{34}N_2O_2S$: Calculated: C, 67.65; H, 8.77; N, 7.17; Found: C, 67.43; H, 8.55; N, 6.98.

30. 5-{[3,5-bis(1,1-dimethylethyl)-4-hydroxyphenyl]-methylene}-3-[2-(2-hydroxyethylamino)ethyl]-4-thiazolidinone, 59% yield, m.p. 174°–176° C.

Utilizing the procedures set forth herein the following additional compounds were prepared.

EXAMPLE 31

5-{[3,5-bis(1,1-dimethylethyl)-4-hydroxyphenyl]methylene}-3-[2-(methyl-2-propynylamino)ethyl]-4-thiazolidinone, m.p. 116°–118° C.

Analysis for $C_{24}H_{34}N_2O_2S$: Calculated: C, 69.53; H, 8.27; N, 6.76; Found: C, 69.27; H, 8.46; N, 6.65.

EXAMPLE 32

5-{[3,5-bis(1,1-dimethylethyl)-4-hydroxyphenyl]methylene}-3-{2-[[2-(dimethylamino)ethyl]amino]ethyl}-4-thiazolidinone, m.p. 245°–249° C. (dec.)

Analysis for $C_{24}H_{39}N_3O_2S$: Calculated: C, 56.90; H, 8.16; N, 8.30; Found: C, 57.12; H, 7.98; N, 8.09.

EXAMPLE 33

5-{[3,5-bis(1,1-dimethylethyl)-4-hydroxyphenyl]methylene}-3-{2-[(phenylmethyl)amino]ethyl}-4-thiazolidinone hydrochloride, m.p. 254°–259° C. (dec.)

Analysis for $C_{27}H_{36}N_2O_2S$: Calculated: C, 66.30; H, 7.63; N, 5.73; Found: C, 66.46; H, 7.53; N, 5.80.

EXAMPLE 34

5-{[3,5-bis(1,1-dimethylethyl)-4-hydroxyphenyl]methylene}-3-[3-(methylamino)propyl]-4-thiazolidinone, m.p. 177°–180° C.

Analysis for $C_{22}H_{34}N_2O_2S$: Calculated: C, 67.65; H, 8.77; N, 7.17; Found: C, 67.72; H, 8.94; N, 7.00.

EXAMPLE 35

5-{[3,5-bis(1,1-dimethylethyl)-4-hydroxyphenyl]methylene}-3-(2-hydroxyethyl)-4-thiazolidinone, m.p. 131°–135° C.

Analysis for $C_{20}H_{29}NO_3S$: Calculated: C, 66.08; H, 8.04; N, 3.85; Found: C, 66.36; H, 8.13; N, 3.87.

EXAMPLE 36

5-{[3,5-bis(1,1-dimethylethyl)-4-hydroxyphenyl]methylene}-3-[(4-methoxyphenyl)methyl]-4-thiazolidinone, m.p. 129°–130° C.

Analysis for $C_{26}H_{33}NO_3S$: Calculated: C, 71.04; H, 7.57; N, 3.19; Found: C, 70.75; H, 7.69; N, 3.18.

EXAMPLE 37

5-{[3,5-bis(1,1-dimethylethyl)-4-hydroxyphenyl]methylene}-3-[2-(propylamino)ethyl]-4-thiazolidinone, m.p. 155°–158° C.

Analysis for $C_{23}H_{36}N_2O_2S$: Calculated: C, 68.28; H, 8.97; N, 6.92; Found: C, 68.38; H, 9.17; N, 7.13.

EXAMPLE 38

5-{[3,5-bis(1,1-dimethylethyl)-4-hydroxyphenyl]methylene}-4-oxo-3-thiazolidineacetonitrile 7.03 g of 5-{[3,5-Bis(1,1-dimethylethyl)-4-hydroxyphenyl]methylene}-4-thiazolidinone and 2.64 g of bromoacetonitrile were reacted in the presence of 0.97 g of 60% sodium hydride in mineral oil and 330 ml of tetrahydrofuran. Work-up of the reaction mixture provided 3.21 g of the desired title product, m.p. 168°–188° C.

Analysis for $C_{20}H_{26}N_2O_2S$: Calculated: C, 67.01; H, 7.31; N, 7.81; Found: C, 66.80; H, 7.36; N, 7.67.

EXAMPLE 39

5-{[3,5-bis(1,1-dimethylethyl)-4-hydroxyphenyl]methylene}-3-(1H-tetrazol-5-ylmethyl)-4-thiazolidinone The title compound was prepared from the nitrile of Example 38 by treatment with tri-N-butyl azide in ethylene glycol dimethyl ether, melting point 260°–263° C. (dec.)

Analysis for $C_{20}H_{27}N_5O_2S$: Calculated: C, 59.83; H, 6.78; N, 17.44; Found: C, 59.93; H, 6.82; N, 17.32.

EXAMPLE 40

5-{[3,5-bis(1,1-dimethylethyl)-4-hydroxyphenyl]methylene}-3-(ethylmethylamino)-4-thiazolidinone A. Preparation of nitrosomethylethylamine 70.15 g of methylethylamine was maintained at 10° C. on an ice bath. To this was added 104 ml of concentrated hydrochloric acid (dropwise with stirring). The addition of the hydrochloric acid was continued at a rate which maintained the reaction temperature at about 15° C. Upon completion of the acid addition, 90 g of sodium nitrite was added to the reaction in small portions. Upon dissolution of the sodium nitrite, a gas formed and the temperature of the reaction mixture dropped to about 0° C. The mixture was placed in an oil bath and heated to about 70° C. during completion of the sodium nitrite addition. After about 90 minutes, gas evolution had ceased and an additional 10 ml of concentrated hydrochloric acid was added generating additional gas evolution. Upon further stirring, an additional 5 ml of concentrated hydrochloric acid was added. The reaction mixture was allowed to stir overnight, with cooling, after which the resultant layers were separated. The upper layer was extracted with a 100 ml portion of diethyl ether followed by a second extraction with an additional 50 ml of diethyl ether. The extracts were combined and evaporated on a steam bath to yield 26.8 g of the desired subtitled intermediate.

B. Preparation of N,N-methylethylhydrazine

To a stirred mixture of 46.75 g nitrosomethylethylamine, 588 ml of water and 133.9 g of zinc dust was added (dropwise) 159 ml of acetic acid. The addition was completed over approximately two hours, and the reaction mixture was maintained at 25°–30° C. The reaction mixture was then heated to about 90° C., allowed to cool after about 30 minutes to 60° C., allowed to cool to room temperature and then filtered. The aqueous filtrate was then cooled in an ice bath and adjusted to pH 11 with 50% sodium hydroxide. A white precipitate formed which made additional stirring difficult. The white suspension was filtered and washed with two portions of water. The original filtrate and the first wash were combined for distillation. The mixture was heated and various fractions collected over a temperature range of about 67° C. to 99° C., each of which contained the desired subtitled intermediate.

C. Preparation of S-carboxymethyl-N'-dithiocarboxy N-methyl-N-ethylhydrazine

N,N-Methylethylhydrazine (13.3 g) and 20 ml of ethanol were cooled in an ice/water bath. To this was added a mixture of 4.69 ml of carbon disulfide and 15.6 ml of diethyl ether, dropwise, with stirring over a period of about 13 minutes. The resultant yellow solution was stirred for an additional 15 minutes at 0° C. and then removed from the ice bath. Additional diethyl ether was added to induce the formation of a precipitate. When the total volume reached 125 ml (due to addition of diethyl ether) two layers had formed. Within about 10 minutes the oily lower layer began to crystallize and the reaction mixture was allowed to stand at room temperature overnight. The reaction mixture was then maintained at 5° C. for two hours prior to filtering. The mixture was filtered, washed with diethyl ether, dried under vacuum at room temperature for three hours and then added to a stirred, cooled (4° C.) mixture of 5.66 g of chloroacetic acid in 12 ml of 5N sodium hydroxide. The reaction mixture was then removed from the ice bath, allowed to warm to room temperature with stirring for 45 minutes, and then added over a period of about 2 minutes to 31.2 ml of 6N hydrochloric acid heated to 85° C. The mixture was warmed to 90° C. over approximately 10 minutes and allowed to cool while stirring to room temperature overnight. A precipitate formed which was filtered, washed lightly with cold water and allowed to air dry for about 15 minutes. The precipitate was then dried under vacuum at 80° C. for three days to yield 4.64 g of the desired subtitled intermediate. The filtrate was stirred at room temperature for 3 days and additional precipitate formed which was subsequently filtered, washed lightly with water and dried under vacuum at 80° C. for 24 hours to yield an additional 1.76 g of the desired subtitled intermediate.

D. Preparation of 5-{[3,5-bis(1,1-dimethylethyl)-4-hydroxyphenyl]methylene}-3-(ethylmethylamino)-2-thioxo-4-thiazolidinone Under nitrogen atmosphere, 6.40 g of the intermediate prepared in Example 40C, 154 ml of acetic acid and 8.82 g of sodium acetate were stirred for 10 minutes. 7.2 g of 3,5-bis(1,1-dimethylethyl)-4-hydroxybenzaldehyde was added and the resultant mixture was heated at reflux temperature for 23 hours and poured into a 400 ml mixture of ice/water with stirring. The resultant mixture was stirred for an additional 20 minutes, filtered and washed with a volume of water to give the desired subtitled intermediate. This intermediate was dried under vacuum at 100° C. for three days, after which it was dissolved in 45 ml of ethanol on a steam bath and diluted with water dropwise while stirring until cloudiness persisted. This mixture was then stirred for an additional five minutes, allowed to cool to room temperature overnight and dried under vacuum at 80° C. for four hours to render 6.99 g of the desired subtitled intermediate.

E. Preparation of 5-{[3,5-bis(1,1-dimethylethyl)-4-hydroxyphenyl]methylene}-3-(ethylmethylamino)-4-thiazolidinone 7.02 g of 5-{[3,5-bis(1,1-dimethylethyl)-4-hydroxyphenyl]methylene}-3-(ethylmethylamino)-2-thioxo-4-thiazolidinone (from Example 40D) and 86.3 ml of toluene were stirred and heated to 60° C. under a nitrogen atmosphere. To this was added 18.6 ml of tri-n-butyl tin hydride and 0.43 g of AIBN. The resultant mixture was heated to reflux temperature for 30 minutes. At that time an additional 0.43 g of AIBN was added. The resultant mixture was heated at reflux temperature for an additional 30 minutes, cooled and transferred to a separatory funnel. To this was added 100 ml of 1N hydrochloric acid and 100 ml of ethyl acetate. The resultant mixture was shaken and separated. The organic layer was washed with brine, dried over sodium sulfate, filtered, evaporated and subsequently chased with chloroform to give an orange/red oil which was taken up in 50 ml of chloroform and filtered. The filtrate was chromatographed on a silica gel column using an 8000 ml gradient of 10–40% ethyl acetate in hexane. Those fractions identified as containing product were evaporated and chased with chloroform. To these fractions were added 15 ml of hexane and the resultant solution was heated slightly. A precipitate formed which was diluted to about 25 ml with additional hexane. The resultant mixture was triturated for about 2 hours, filtered and then washed with hexane to yield 1.94 g of the desired product, m.p. 133.5°–135° C.

Analysis for $C_{21}H_{32}N_2O_2S$: Calculated: C, 66.98; H, 8.57; N, 7.44; Found: C, 66.97; H, 8.80; N, 7.24.

Utilizing the procedures substantially as described in Example 40 and described elsewhere herein, the following additional compounds were prepared.

EXAMPLE 41

5-{[3,5-bis(1,1-dimethylethyl)-4-hydroxyphenyl]methylene}-3-(butylmethylamino)-4-thiazolidinone, m.p. 128.5°–131° C.

Analysis for $C_{23}H_{36}N_2O_2S$: Calculated: C, 68.28; H, 8.97; N, 6.92; Found: C, 68.45; H, 9.00; N, 6.70.

EXAMPLE 42

5-{[3,5-bis(1,1-dimethylethyl)-4-hydroxyphenyl]methylene}-3-[(2-phenylethyl)methylamino]-4-thiazolidinone, m.p. 93°–97° C.

Analysis for $C_{27}H_{36}N_2O_2S$: Calculated: C, 71.64; H, 8.02; N, 6.19; Found: C, 71.48; H, 8.30; N, 5.81.

EXAMPLE 43

5-{[3,5-bis(1,1-dimethylethyl)-4-hydroxyphenyl]methylene}-3-(4-methyl-1-piperazinyl)-4-thiazolidinone, m.p. 221°–225° C.

Analysis for $C_{23}H_{34}N_2O_2S$: Calculated: C, 66.15; H, 8.45; N, 10.06; Found: C, 66.10; H, 8.36; N, 9.81.

EXAMPLE 44

5-{[3,5-bis(1,1-dimethylethyl)-4-hydroxyphenyl]methylene}-3-(1-piperidinyl)-4-thiazolidinone, m.p. 213°–215° C.

Analysis for $C_{23}H_{34}N_2O_2S$: Calculated: C, 68.62; H, 8.51; N, 6.96; Found: C, 68.41; H, 8.49; N, 7.26.

EXAMPLE 45

5-{[3,5-bis(1,1-dimethylethyl)-4-hydroxyphenyl]methylene}-3-(4-morpholinyl)-4-thiazolidinone, m.p. 226°–228° C.

Analysis for $C_{22}H_{32}N_2O_3S$: Calculated: C, 65.31; H, 7.97; N, 6.92; Found: C, 65.59; H, 7.94; N, 7.20.

EXAMPLE 46

5-{1-[3,5-bis(1,1-dimethylethyl)-4-hydroxyphenyl]methylmethylene}-3-(dimethylamino)-4-thiazolidinone A. Preparation of 1-[3,5-bis(1,1-dimethylethyl)-4-hydroxyphenyl]ethanone Under a nitrogen atmosphere, 6.89 ml of acetylchloride and 14.75 ml of stannic chloride were dissolved in 200 ml of methylene chloride and chilled to −4° C. To this was added 20 g of 2,6-di-t-butylphenol (in 100 ml of methylene chloride) over 10 minutes. The resultant mixture was stirred for 30 minutes at 0° C., then poured into a mixture of 400 ml of ice and 1N hydrochloric acid and stirred. The mixture separated into layers which were subsequently separated. The organic layer was washed with 100 ml of saturated sodium bicarbonate and 100 ml of brine. The organic layer was dried and the solvent evaporated to give 23.39 g of the desired subtitled intermediate.

B. Preparation of 5-{1-[3,5-bis(1,1-dimethylethyl)-4-hydroxyphenyl]methylmethylene}-3-(dimethylamino)-2-thioxo-4-thiazolidinone To 675 ml of toluene were added 20.9 g of 1-[3,5-bis-(1,1-dimethylethyl)-4-hydroxyphenyl]ethanone, 13.3 g of N-dimethylaminorhodanine 6.5 g of ammonium acetate and about 20 ml of acetic acid. The mixture was heated at reflux temperature and any aqueous layer generated was collected in a Dean-Stark trap. Over the following 52 hours an additional 39 g of ammonium acetate and about 100 mi of acetic acid were added in increments and a total of 89.2 ml of aqueous phase was drawn off. Following workup by conventional techniques, 17.1 g of the desired subtitled intermediate was recovered.

C. Preparation of 5-{1-[3,5-bis(1,1-dimethylethyl)-4-hydroxyphenyl]methylmethylene}-3-(dimethylamino)-4-thiazolidinone Utilizing the procedure set forth in Example 40E, reduction of the thione was effected utilizing tri-n-butyl tin hydride and AIBN in toluene to render the desired title compound, m.p. 181°–186° C.

Analysis for $C_{21}H_{32}N_2O_2S$: Calculated: C, 66.98; H, 8.57; N, 7.44; Found: C, 66.84; H, 8.48; N, 7.39.

EXAMPLE 47

5-{[3,5-bis(1,1-dimethylethyl)-4-hydroxyphenyl]methylene}-3-(methylamino)-4-thiazolidinone A. Preparation of benzaldehydemethylhydrazone 50.8 ml of benzaldehyde (500 mmol) and 26.5 ml (500 mmol) of methylhydrazine were dissolved in 1 l of methanol. The mixture was stirred together at room temperature for 75 minutes and then stripped of solvent to give 67.8 g of the desired subtitled intermediate.

B. Preparation of benzaldehyde N-methyl, N-2-propenylhydrazone 67.8 g of benzaldehydemethylhydrazone (as prepared in Example 47A, above), 60.5 g of allyl bromide and 50.5 g of triethlyamine were dissolved in 1 l of acetonitrile and the mixture was heated at reflux temperature for 16 hours, then cooled. An additional 45 g of allyl bromide and 38 g of triethylamine were added and the mixture was again heated at reflux for an additional 7 hours, allowed to cool and then stripped of solvent to yield 268 g of a residue. To this residue was added 500 ml of THF and the resultant mixture was shaken, filtered and washed with an additional 125 ml of THF. The filtrate was stripped of solvent to yield 67 g of the desired subtitled intermediate.

C. Preparation of N-methyl, N-2-propenylhydrazine 59.9 g of benzaldehyde N-methyl, N-2-propenylhydrazone (prepared as described in Example 47B, above), 44 g of hydrazine and 137 ml of ethanol were heated at reflux temperature for 21.5 hours and allowed to cool. The reflux condenser was replaced with a distillation head and the mixture was distilled at atmospheric pressure. The first three distillates were collected, combined and 100 ml of 1N HCl were added. An additional 100 ml of concentrated HCl was added, with ice, and the resultant mixture separated and washed with a small amount of ethyl acetate. The resultant layers were separated and the water distilled off until solids clogged the stir bar. The solids were filtered off and the filtrate was stripped and added to 125 ml of chilled 50% NaOH. The resulting solid was filtered off and discarded. The filtrate contained two layers which were separated. The top layer contained the desired subtitled intermediate and the bottom, aqueous layer was extracted with diethyl ether which, upon stripping, gave additional product.

D. Preparation of N-Methyl, N-3-propenyl-5-carboxymethyl-dithiocarbamate

To 12.67 g of N-methyl, N-2-propenylhydrazine (prepared as described in Example 47C) in 23 ml of ethanol chilled to 0° C. was added a solution of 11.18 g of carbon disulfide in 26 ml of diethyl ether. The resultant mixture was removed from the ice bath and allowed to stand at room temperature for about 15.5 hours, after which the solvent was stripped to yield a residue of approximately 36.5 g. To this residue was added 13.9 g of chloroacetic acid dissolved in 29.5 ml of 5N NaOH (chilled in an ice bath). The resultant solution was allowed to stand for 3 hours at room temperature. The pH of the solution was reduced to about 3 by the addition of 8 ml of concentrated hydrochloric acid. To this was added 50 ml of diethyl ether, resulting in a three phase separation. The aqueous phases were pooled and extracted with an additional 50 ml of chloroform, then stripped of solvent to yield approximately 40.4 g of the desired subtitled intermediate.

E. Preparation of 5-{[3,5-bis(1,1-dimethylethyl)-4-hydroxyphenyl]methylene}-2-thioxo-3-(methyl-2-propenylamino)-4-thiazolidinone 29.3 g of 3,5-di-tert-butyl-4-hydroxybenzaidehyde, 38.8 g of the intermediate prepared as described in Example 47D, above, and 40.34 g of sodium acetate were mixed in 810 ml of acetic acid and the resultant solution was heated at reflux temperature for 24 hours. The solution was then allowed to cool and stirred for an additional 60 hours at room temperature. The solution was then poured into 2 l of ice water, separated and washed with an additional volume of water to yield about 44 g of the desired subtitled intermediate.

F. Preparation of 5-{[3,5-bis(1,1-dimethylethyl)-4-hydroxyphenyl]methylene}-3-(methyl-2-propenylamino)-4-thiazolidinone Utilizing the procedure described in Example 40E, and elsewhere herein, 42.8 g of the thione of Example 47E, above, was reduced to the desired subtitled intermediate (8.34 g).

G. Preparation of 5-{[3,5-bis(1,1-dimethylethyl)-4-hydroxyphenyl]methylene}-3-(methylamino)-4-thiazolidinone 6.11 g of the subtitled intermediate of Example 47F was dissolved in a mixture of 135 ml ethanol and 15.3 ml of water and the mixture heated to 70° C. 50 mg of tris-(triphenylphosphine)rhodium (I) chloride was added and the mixture heated at reflux temperature for 50 minutes, after which an additional 550 mg of the catalyst was added followed by heating at reflux temperature for an additional 2.5 hours. The mixture was cooled, stirred at room temperature overnight and stripped of solvent to give 2.05 g of the desired product after further workup, m.p. 151°–153.5° C.

Analysis for $C_{19}H_{28}N_2O_2S$: Calculated: C, 65.86; H, 7.56; N, 8.09; Found: C, 65.67; H, 7.81; N, 8.34.

Utilizing the procedures set forth herein, the following additional compounds were prepared.

EXAMPLE 48

5-{1-[3,5-bis(1,1-dimethylethyl)-4-hydroxyphenyl]-methylmethylene}-4-thiazolidinone, m.p. >230° C.

Analysis for $C_{19}H_{27}N_1O_2S$: Calculated: C, 68.43; H, 8.16; N, 4.20; Found: C, 68.60; H, 8.28; N, 4.17.

EXAMPLE 49

5-{[3,5-bis(1,1-dimethylethyl)-4-hydroxyphenyl]methylene}-3-[(2-(4-morpholinyl)ethyl]amino-4-thiazolidinone, m.p. 218°–222° C. (dec.)

Analysis for $C_{24}H_{36}N_2O_3S$: Calculated: C, 66.83; H, 8.39; N, 6.48; Found: C, 66.58; H, 8.15; N, 6.67.

EXAMPLE 50

3-amino-5-{[3,5-bis(1,1-dimethylethyl)-4-hydroxyphenyl]methylene}-4-thiazolidinone, m.p. 162°–164° C.

Analysis for $C_{18}H_{26}N_2O_2S$: Calculated: C, 64.64; H, 7.84; N, 8.38; Found: C, 64.85; H, 7.92; N, 8.19.

EXAMPLE 51

5-{[3,5-bis(1,1-dimethylethyl)-4-hydroxyphenyl]methylene}-3-(propylamino)-4-thiazolidinone, m.p. 131°–136° C.

Analysis for $C_{21}H_{32}N_2O_2S$: Calculated: C, 66.98; H, 8.57; N, 7.44; Found: C, 67.22; H, 8.70; N, 7.37.

EXAMPLE 52

5-{[3,5-bis (1,1-dimethylethyl )-4-hydroxyphenyl]methylene}-3-(ethylamino)-4-thiazolidinone, m.p. 125°–127° C.

Analysis for $C_{20}H_{30}N_2O_2S$: Calculated: C, 66.26; H, 8.34; N, 7.73; Found: C, 66.46; H, 8.35; N, 7.95.

EXAMPLE 53

5-{[3,5-bis(1,1-dimethylethyl)-4-hydroxyphenyl]methylene}-3-(dimethylamino)-2-thioxo-4-thiazolidinone, m.p. 158°–160° C.

Analysis for $C_{20}H_{28}N_2O_2S_2$: Calculated: C, 61.19; H, 7.19; N, 7.14; Found: C, 61.33; H, 7.23; N, 7.43.

EXAMPLE 54

5-{[3,5-bis(1,1-dimethylethyl)-4-hydroxyphenyl]methylene}-3-[2-(propylamino)ethyl]-4-thiazolidinone, m.p. 155°–158° C.

Analysis for $C_{23}H_{36}N_2O_2S$: Calculated: C, 68.28; H, 8.97; N, 6.92; Found: C, 68.38; H, 9.17; N, 7.13.

EXAMPLE 55

5-{[3,5-bis(1,1-dimethylethyl)-4-hydroxyphenyl]methylene}-3-[(2-hydroxyethyl)amino]-4-thiazolidinone, m.p. 128°–132° C.

Analysis for $C_{20}H_{30}N_2O_3S$: Calculated: C, 63.46; H, 7.99; N, 7.40; Found: C, 63.57; H, 7.92; N, 7.45.

EXAMPLE 56

5-[(3,5-di-2-propenyl-4-hydroxyphenyl)methylene]-4-thiazolidinone

A. Preparation of 3,5-di-(2-propenyl)-4-hydroxybenzaldehyde

Under a nitrogen atmosphere and using a mechanical stirrer, 250 g of parahydroxybenzaldehyde, 247.6 g of allyl bromide, 311.7 g of potassium bicarbonate and 650 ml of acetone were heated to reflux temperature for about 18 hours. The mixture was allowed to cool, after which about 1 l of water was added followed by extraction with two 800 ml portions of diethyl ether. Subsequent distillation of the organic phase rendered about 299 g of 4-(2-propenyl)oxybenzaldehyde which was then heated with about 300 ml of diethylaniline for 5.5 hours at 195°–205° C. The mixture was cooled and 750 ml of ethyl acetate was added. The mixture was washed with three 500 ml portions of 1N HCl which, followed by subsequent workup, yielded about 138 g of 3-(2-propenyl)-4-hydroxybenzaldehyde. The mono-substituted aldehyde (159 g) was again heated to reflux with 152 g of potassium carbonate and 465 ml of acetone for 3 hours and then allowed to cool. The mixture was poured into 900 ml of ice water and subsequently extracted with two 430 ml portions of diethyl ether to yield about 170 g of 3-(2-propenyl)-4-(2-propenyloxy)-benzaldehyde. The di-substituted aldehyde was then heated in about 500 ml of diethylaniline, under a nitrogen atmosphere, to 195°–205° C. for about 6.5 hours. The mixture was cooled and dissolved in about 800 ml of ethyl acetate, washed with three 1 l portions of 1N HCl and, following workup, rendered about 121.9 g of the desired subtitled intermediate.

B. Preparation of 5-[(3,5-di-2-propenyl-4-hydroxyphenyl)methylene]-4-thiazolidinone 3,5-di-(2-propenyl)-4-hydroxybenzaldehyde (50.5 g), 36.6 g of rhodanine and 164 g of sodium acetate were heated together at reflux temperature in 1.25 liter of acetic acid for 14.5 hours. The resultant solution was cooled, poured into 2 l of ice water to yield, upon separation, about 75 g of 5-[(3,5-di-2-propenyl-4-hydroxyphenyl)methylene]-2-thioxo-4-thiazolidinone, m.p. 157°–160° C.

The thione produced above was reduced by treating with zinc dust and hydrochloric acid in ethanol under nitrogen to yield, after workup, about 39 g of the desired titled product, m.p. 184°–188° C.

Analysis for $C_{16}H_{17}NO_2S$: Calculated: C, 66.87; H, 5.96; N, 4.87; Found: C, 66.62; H, 5.92; N, 4.89.

Utilizing the procedures set forth in Example 56 and elsewhere herein, the following additional compounds were prepared.

EXAMPLE 57

5-[(3,5-di-2-propenyl-4-hydroxyphenyl)methylene]-3-methyl-4-thiazolidinone, m.p. 155°–159° C.

Analysis for $C_{17}H_{19}NO_2S$: Calculated: C, 67.74; H, 6.35; N, 4.65; Found: C, 67.53; H, 6.09; N, 4.45.

EXAMPLE 58

5-[(3,5-dipropyl-4-hydroxyphenyl)methylene]-3-methyl-4-thiazolidinone, m.p. 162°–165° C.

Analysis for $C_{17}H_{23}NO_2S$: Calculated: C, 66.85; H, 7.59; N, 4.59; Found: C, 67.12; H, 7.37; N, 4.52.

EXAMPLE 59

5-[(3,5-dipropyl-4-hydroxyphenyl)methylene]-4-thiazolidinone, m.p. 202°–205° C.

Analysis for $C_{16}H_{23}NO_2S$: Calculated: C, 65.95; H, 7.26; N, 4.81; Found: C, 66.16; H, 7.49; N, 4.79.

EXAMPLE 60

5-{[3-(1,1-dimethylethyl)-4-hydroxy-5-methylphenyl]methylene}-4-thiazolidinone.

A. Preparation of 3-(1,1-dimethylethyl)-4-hydroxy-5-methylbenzaldehyde

Under a nitrogen atmosphere, 76.65 g of 2-(1,1-dimethylethyl)-6-methylphenol (Aldrich), 65.42 g of hexamethylenetetramine and 700 ml of trifluoroacetic acid were stirred at reflux temperature for about 24 hours, then allowed to cool and evaporated. The residue from the evaporation was taken up in 1500 ml of water and 1000 ml of chloroform and neutralized to pH 7 with solid sodium carbonate. The resultant layers were separated and the aqueous layer was washed with chloroform. The organic layer was dried over sodium sulfate overnight, after which it was again washed with a volume of chloroform and evaporated. The resultant residue was then taken up in 375 ml of toluene, heated on a steam bath and then allowed to cool to room temperature overnight. Subsequent workup gave 28.3 g of the desired subtitled intermediate.

B. Preparation of 5-{[3-(1,1-dimethylethyl)-4-hydroxy-5-methylphenyl]methylene}-2-thioxo-4-thiazolidinone 28.3 g of the intermediate prepared in Example 60A, 24 g of N-aminorhodanine, 48.3 g of sodium acetate in 735 ml of acetic acid were heated to reflux temperature for about 7 hours and then allowed to cool to room temperature with continual stirring overnight. The resultant mixture was poured into 1500 ml of ice water with stirring and then filtered. The wet filter cake was transferred to a beaker and dissolved in a mixture of ethyl acetate and water and then separated. The organic layer was dried over sodium sulfate, filtered and then washed with ethyl acetate. Further workup, followed by trituration in hot chloroform and subsequent drying under vacuum, rendered about 18 g of the desired subtitled intermediate, m.p. 210°–216° C.

C. Preparation of 5-{[3-(1,1-dimethylethyl)-4-hydroxy-5-methylphenyl]methylene}-4-thiazolidinone.

Reduction of the thione of Example 60B as described herein was effected which, following workup, rendered 1.56 g of the titled product, m.p. 162°–165° C.

Analysis for $C_{15}H_{19}NO_2S$: Calculated: C, 64.95; H, 6.90; N, 5.05; Found: C, 65.12; H, 7.05; N, 4.99.

Utilizing the procedures set forth in Example 60 and elsewhere herein, the following additional compounds were prepared.

EXAMPLE 61

3-amino-5-{[3-(1,1-dimethylethyl)-4-hydroxy-5-methylphenyl]methylene}-4-thiazolidinone, m.p. 110° C. (dec.)

Analysis for $C_{15}H_{20}N_2O_2S$: Calculated: C, 61.81; H, 7.29; N, 9.01; Found: C, 61.90; H, 7.47; N, 8.78.

EXAMPLE 62

5-{[3-(1,1-dimethylethyl)-4-hydroxy-5-methylphenyl]methylene}-3-dimethylamino-2-thioxo-4-thiazolidinone, m.p. 189°–190° C.

Analysis for $C_{17}H_{22}N_2O_2S$: Calculated: C, 58.26; H, 6.33; N, 7.99; Found: C, 58.55; H, 6.08; N, 8.28.

EXAMPLE 63

5-{[3-(1,1-dimethylethyl)-4-hydroxy-5-methylphenyl]methylene}-3-methyl-4-thiazolidinone, m.p. 192°–195° C.

Analysis for $C_{16}H_{21}NO_2S$: Calculated: C, 65.95; H, 7.26; N, 4.81; Found: C, 66.24; H, 7.17; N, 5.02.

EXAMPLE 64

5-{[3-(1,1-dimethylethyl)-4-hydroxy-5-methylphenyl]methylene}-3-dimethylamino-4-thiazolidinone, m.p. 182°–192° C.

Analysis for $C_{17}H_{24}N_2O_2S$: Calculated: C, 63.72; H, 7.55; N, 8.74; Found: C, 63.45; H, 7.58; N, 8.93.

EXAMPLE 65

5-{[3,5-bis[3-(acetyloxy)propyl]-4-hydroxyphenyl]methylene}-3-methyl-4-thiazolidinone

A. Preparation of 3,5-di(3-trifluoroacetyloxypropyl)-4-hydroxybenzaldehyde 200 g of 3-(2-hydroxyphenyl)propene, 226 g of potassium carbonate and 180 g of allyl bromide were stirred in 490 ml of acetone at reflux temperature for 23 hours and then cooled. One liter of water was added and the resultant layers were separated. The aqueous layer extracted with two volumes of diethyl ether, dried and stripped of solvent to give 256 g of 3-(2-propenyloxyphenyl)propene which was subsequently rearranged as described in Example 56 to the 2,6-di-propenylphenol intermediate. 52.2 g of said intermediate was dissolved in 500 ml of THF and chilled to −5° C. 300 ml of one molar borane was added over 15 minutes (maximum temperature not exceeding 18° C.), after which the mixture was stirred for 36 hours and chilled to 0° C. 80 ml of water was added over a 5 minute period, after which 120 ml of 5N sodium hydroxide was added all at once. When the temperature of the reaction mixture reached 1° C., 81 ml of 30% hydrogen peroxide was added over a 25 minute period and the mixture stirred for one hour and then concentrated. An additional 500 ml of water and 250 ml of ethyl acetate were added which, following workup, gave about 54 g of the desired 2,6-di(3-hydroxypropyl)phenol intermediate, m.p. 176°–187° C.

30.48 g of said 2,6-di(3-hydroxypropyl)phenol, 20.33 g of hexamethylenetetramine and 220 g of trifluoroacetic acid were heated at reflux temperature for 17 hours after which the mixture was cooled and concentrated. A volume of acetonitrile was added and then stripped and subsequently repeated to provide a residue. The residue was dissolved in 500 ml of ethyl acetate which was then washed with 250 ml of water and four 250 ml volumes of a saturated sodium bicarbonate solution. Following workup, about 56 g of the desired subtitled intermediate was obtained.

B. Preparation of
5-{[3,5-bis[3-(acetyloxy)propyl]-4-hydroxyphenyl]methylene}-3-methyl-2-thioxo-4-thiazolidinone.

25 g of the intermediate prepared in Example 65A, 11.2 g of N-methylrhodanine and 19 g of sodium acetate were heated at reflux temperature in 300 ml of acetic acid for 16.5 hours. The mixture, allowed to cool to room temperature for 6 hours was filtered and then washed with acetic acid. Further workup rendered the subtitled intermediate, m.p. 151°–155° C.

C. Preparation of
5-{[3,5-bis[3-(acetyloxy)-propyl]-4-hydroxyphenyl]methylene}-3-methyl-4-thiazolidinone.

Utilizing the procedures set forth herein, the thione intermediate prepared in Example 65B was reduced by the action of tri-n-butyl tin hydride and AIBN to yield the desired titled product, m.p. 112°–116° C.

Analysis for $C_{21}H_{27}NO_6S$: Calculated: C, 59.84; H, 6.46; N, 3.32; Found: C, 60.05; H, 6.58; N, 3.30.

Utilizing the procedures set forth in Example 65, and elsewhere herein, the following compounds were prepared.

EXAMPLE 66

5-{[3,5-bis[3-(acetyloxy)propyl]-4-hydroxyphenyl]methylene}-3-(dimethylamino)-4-thiazolidinone, m.p. 108°–110° C.

Analysis for $C_{22}H_{30}N_2O_6S$: Calculated: C, 58.65; H, 6.71; N, 6.22; Found: C, 58.80; H, 6.76; N, 6.17.

EXAMPLE 67

5-{[3-(1,1-dimethylethyl)-4-hydroxy-5-propylphenyl]methylene}-3-methyl-4-thiazolidinone, m.p. 189.5°–191.5° C.

Analysis for $C_{18}H_{25}NO_2S$: Calculated: C, 67.68; H, 7.89; N, 4.38; Found: C, 67.97; H, 8.16; N, 4.40.

EXAMPLE 68

5-{[3-(1,1-dimethylethyl)-4-hydroxyphenyl]methylene}3-methyl-4-thiazolidinone

A. Preparation of
3-(1,1-dimethylethyl)-4-hydroxybenzaldehyde

Into 101.5 g of N-methylformanilide was added dropwise with cooling 107 g of phosphoryl chloride over a period of 15 minutes. The mixture was allowed to warm to room temperature and stirred for 70 minutes. 67.5 g of ortho-t-butylphenol was added and stirred for about 45 minutes after which the mixture was heated to about 50°–60° C. and allowed to stir for 4.5 hours. The reaction mixture was poured into a volume of crushed ice and extracted with chloroform. The aqueous layer was separated and washed again with chloroform. The chloroform layers were combined and extracted with 2000 ml of a 5% potassium hydroxide solution. The aqueous potassium hydroxide layer was separated and added to 1000 ml of chloroform. The pH of the resulting two-phase mixture was adjusted to 3 with concentrated hydrochloric acid with stirring. The resultant layers were separated and the aqueous layer was again extracted with chloroform and dried over sodium sulfate overnight to give 18.1 g of the desired subtitled intermediate.

B. Preparation of
5-{[3-(1,1-dimethylethyl)-4-hydroxyphenyl]methylene}-3-methyl-2-thioxo-4-thiazolidinone The benzaldehyde intermediate from Example 68A (17.5 g) was dissolved in 490 ml of acetic acid. The resulting solution was added to a mixture of 14.45 g of N-methylrhodanine and 28.18 g of sodium acetate. The resultant suspension was heated, stirred at reflux temperature for 24 hours (at which time a yellow precipitate had formed), filtered and washed with acetic acid and diethyl ether. The precipitate was triturated with 300 ml of diethyl ether, filtered, washed again with diethyl ether and triturated yet a second time with 600 ml of water. Drying the resultant solid in vacuo yielded the desired subtitled intermediate, m.p. >230° C.

C. Preparation of 5-{[3-(1,1-dimethylethyl)-4-hydroxyphenyl]methylene}-3-methyl-4-thiazolidinone The thione prepared in Example 68B was reduced as described above utilizing tri-n-butyl tin hydride and AIBN to the desired title product, m.p. >230° C.

Analysis for $C_{15}H_{19}NO_2S$: Calculated: C, 64.95; H, 6.90; N, 5.05; Found: C, 65.07; H, 7.02; N, 5.28.

Utilizing the procedures set forth herein, the following additional compounds were prepared.

EXAMPLE 69

5-{[3,5-bis(1,1-dimethylethyl)-4-hydroxyphenyl]methylene}-2,4-thiazolidinedione, m.p. 234°–238° C.

Analysis for $C_{18}H_{23}NO_3S$: Calculated: C, 64.83; H, 6.95; N, 4.20; Found: C, 64.77; H, 6.73; N, 3.93.

EXAMPLE 70

5-[(4-hydroxy-3,5-dimethylphenyl)methylene]-3-methyl-4-thiazolidinone, m.p. 207°–212° C. (dec.)

Analysis for $C_{13}H_{15}NO_2S$: Calculated: C, 62.62; H, 6.06; N, 5.62; Found: C, 62.58; H, 6.05; N, 5.65.

EXAMPLE 71

3-{[3,5-bis(1,1-dimethylethyl)-4-hydroxyphenyl]methylene}-2-pyrrolidinone

Under a nitrogen atmosphere, 1.52 ml of 2-pyrrolidinone was added to a solution of 32 ml of 2M magnesium methyl carbonate in DMF and 5.86 g of 3,5-di-tert-butyl-4-hydroxybenzaldehyde. The resultant mixture was stirred at reflux temperature for six days and then allowed to cool. The cooled reaction mixture was poured into 40 g of ice containing 10 ml concentrated hydrochloric acid and then extracted with chloroform. The chloroform layer was collected, filtered and the filtrate was concentrated. The resulting residue was purified by silica gel chromatography and recrystallized from ethyl acetate to give the desired titled product (21% yield), m.p. 216°–218° C.

Analysis for $C_{19}H_{27}NO_2$: Calculated: C, 75.71; H, 9.03; N, 6.05; Found: C, 75.95; H, 9.08; N, 4.66.

EXAMPLE 72

3-{[3,5-bis(1,1-dimethylethyl)-4-hydroxyphenyl]methylene}-1-methyl-2-pyrrolidinone A. Preparation of
3,5-bis(1,1-dimethylethyl)oxypivaloylquinone methide Under a nitrogen atmosphere, 8.2 g of 3,5-di-tert-butyl-4-hydroxybenzaldehyde was dissolved in 350 ml of methylene chloride with stirring. Separately, to a dropping funnel was added an additional 35 ml of methylene chloride followed by 4.74 ml of pivaloyl chloride. To the aldehyde solution was added 3.37 ml of triethylamine after which the dropwise addition of the solution from the dropping funnel was immediately started. The addition was complete in 5 minutes and the resultant mixture was stirred an additional 10 minutes at room temperature and then poured into 350 ml of water, shaken and then separated. The methylene chloride layer was dried with sodium sulfate, filtered and washed with a volume of distilled methylene chloride and evaporated to render the desired subtitled intermediate as a yellow solid.

B. Preparation of 3-{[3,5-bis(1,1-dimethylethyl)-4-hydroxypheny]methylene}-1-methyl-2-pyrrolidinone 39.55 ml of 1.77M n-butyllithium in hexane was added to a cold (0° C.) solution of 9.81 ml of diisopropylamine in 210 ml of THF. After stirring for 15 minutes at 0° C., 6.72 ml of N-methyl pyrrolidinone was added. Stirring was continued for 5 minutes at 0° C. and the solution was then cooled to −78° C., at which time a solution of the intermediate of Example 72A in 175 ml of THF was added over a 10 minute period. After stirring the solution for one hour at −70° C., the reaction was quenched with 1N hydrochloric acid. The reaction mixture was diluted with additional 1N hydrochloric acid and ethyl acetate, shaken and then separated. The organic layer was extracted with a saturated sodium bicarbonate solution and then brine. The organic layer was dried with sodium sulfate, filtered and then evaporated to give 18 g of a red/orange solid. 7.99 g of p-toluene sulfonic acid monohydrate was added to a solution of 18 g of the red/orange solid in 350 ml of toluene and the resultant solution stirred at room temperature for 24 hours. The reaction was filtered and evaporated to give 9.1 g of crude product which was chromatographed on silica gel using a gradient of 10–35% acetone in hexane. Those fractions containing purified product were combined and evaporated to give 3.9 g of the desired titled product, m.p. 187°–188.5° C.

Analysis for $C_{20}H_{29}NO_2$: Calculated: C, 76.15; H, 9.27; N, 4.44; Found: C, 76.36; H, 9.20; N, 4.47.

EXAMPLE 73

5-{[3,5-bis(1,1-dimethylethyl)-4-hydroxyphenyl]methylene}-2-hydroxy-3-methyl-4-thiazolidinone 12.56 g of 5-{[3,5-bis(1,1-dimethylethyl)-4hydroxyphenyl]methylene}-3-methyl-4-thiazolidinone, 1-oxide (the compound of Example 12) was dissolved in 216 ml of methylene chloride and the resultant solution cooled to −78° C. Separately, 6.1 ml of trifluoroacetic anhydride and 72 ml of methylene chloride were placed in a dropping funnel and the solution added dropwise over a 40-minute period (temperature maintained at or below −70° C.) to the previously prepared solution of the compound of Example 12 in methylene chloride. The resulting reaction mixture was stirred at −75° C. for 1 hour, then warmed to 0° C. over 45 minutes, diluted with a volume of methylene chloride, washed with two volumes of water, dried over sodium sulfate and subsequently filtered and evaporated to give 15.8 g of the desired titled product and trace impurities. This product was dissolved in 25 ml of warm ethyl acetate and then added to 450 ml of hexane. As the solution cooled, it became milky and an additional 5 ml of ethyl acetate was added and swirled to clarify. The solution was then allowed to cool to room temperature with precipitate forming overnight. The precipitate was collected by filtration, washed with hexane and dried at room temperature in vacuo overnight. The resultant product was further worked up by adding it to 30 ml of hot ethyl acetate, to which was added an additional 150 ml of hexane. A precipitate began to form. The mixture was allowed to cool to room temperature and stand for 6 hours, after which it was filtered, washed with a volume of hexane and dried in vacuo at 50° C. overnight to render 8.83 g of the desired titled product, m.p. 165°–170° C.

Analysis for $C_{19}H_{27}NO_3S$: Calculated: C, 65.30; H, 7.79; N, 4.01; Found: C, 65.50; H, 7.80; N, 4.02.

As noted previously, the compounds of the present invention are physiologically active as demonstrated in the following test systems.

Carrageenin Assay

The compounds were evaluated for antiinflammatory activity in the test method described by C. A. Winter, Proc. Soc. Exp. Biol. Med., 111, 544 (1962). In this test, inflammation is created by injecting carrageenin into the hind paws of rats. Test compounds are administered prior to injection to determine percent inhibition of the subsequent inflammation in comparison with control animals. The results are reported in Table I.

TABLE I

| Antiinflammatory Activity in the Carrageenin Assay | | |
|---|---|---|
| Compound of Example No. | Dose mg/kg* | Percent Inhibition |
| 1 | 30 | 67% |
| 2 | 50 | 46% |
| 3 | 50 | 12% |
| 4 | 50 | 65% |
| 14 | 50 | 43% |
| 15 | 50 | 42% |
| 16 | 50 | 40% |
| 17 | 50 | 18% |
| 18 | 50 | 22% |

*orally by gavage

Collagen-Induced Arthritis Assay

Type II collagen was isolated from bovine articular cartilage by the method of Strawich and Nimni [Biochemistry, 10, 3905 (1971)]. The collagen was dissolved in 0.1M acetic acid and stored at −20° C. Type II collagen solution was diluted to 2 mg/ml concentration and emulsified thoroughly with an equal volume of incomplete Freund's adjuvant (ICFA). The emulsion containing approximately 0.5 mg of collagen was injected intradermally on day 0 to groups of 6 inbred Lewis male rats (Charles River Breeders; 170–200 g) at various sites in the dorsal area. The hindpaw volumes of each rat were measured and recorded three times a week throughout the test period to assess the inflammatory reaction. The test group animals received compounds under test as suspensions in carboxymethylcellulose vehicle, by oral garage, 5 days per week (Monday–Friday), beginning on day 1. Control animals received vehicle without a test compound. At the end of the test (day 28 or 30), the blood of these animals was drawn by cardiac puncture and the serum anti-type II collagen antibody levels were estimated by passive hemagglutination technique, using glutaraldehyde treated sheep red cells, to which type II collagen is conjugated [Avrameas et al., Immunochemistry, 6, 67 (1969); Andriopoulos et al., Arth. Rheum., 19, 613 (1976)]. The cellular response or delayed-type hypersensitivity response to type II collagen was measured by the radiometric ear index assay [Kostiala, Immunology, 33, 561 (1977)]. In certain experiments, the bone damage occurring because of immunization with type II collagen and the effects of drugs were determined from the radiographs of the hindpaws of two or three representative animals from each group. Injections of ICFA without collagen II were employed in some rats as a negative control; these rats received only carboxymethylcellulose vehicle during the test.

The results of testing the compounds of the present invention in the collagen-induced arthritis system are summarized in Table II. The % inhibition was calculated according to the following formula:

$$\% \text{ inhibition} = \left[ 1 - \frac{Vt - Vv}{Vc - Vv} \right] \times 100$$

where Vt is the hindpaw volume of a compound-treated animal (test group), Vc is the hindpaw volume of a non-compound-treated animal (carboxymethylcellulose vehicle only-the control group), and Vv is the hindpaw volume of a vehicle (carboxymethylcellulose) treated animal which received ICFA with no collagen II (negative control group).

TABLE II

Inhibition of Collagen-Induced Arthritis

| Compound of Example No. | Dose mg/kg* | % inhibition* |
|---|---|---|
| 1 | 50 | 100% |
|   | 50 | 53% |
| 2 | 30 | 91% |
|   | 50 | 100% |
|   | 30 | 50% |
| 3 | 50 | 79% |
| 4 | 50 | 5% |

*See text for experimental method.

Developing Adjuvant-Induced Arthritis Test in Rats

Compounds were tested for their ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135–1141 (1977).

Adjuvant arthritis was induced in male Lewis-Wistar rats (200–210 grams) by a single subplantar injection into the right hind paw of 0.1 ml of a 0.5% suspension of heat-killed, lyophilized *Mycobacterium tuberculosis* (Calbiochem-Perrigen-C) in mineral oil (a modification of a method reported by Winter et al., Arth. Rheum., 9, 394–397 (1966)). One group of 10 rats ("TB control") received only this treatment. Another group of 5 rats received no treatment (normal control). Each compound to be tested was suspended in carboxymethylcellulose (1%) and administered p.o. to rats (groups of 5 each) in daily doses of 50 mg/kg beginning on day one and continuing through the 28th day after the adjuvant injection (29 doses). Paw volumes were measured by mercury displacement using a Statham pressure transducer and digital voltmeter. Volumes of both the injected and the uninjected hind paws were measured on days 16, 18, 21, 23, 25, 28, and 30. X-ray photos were taken on day 30, after the animals were sacrificed. The paw volume measurements on the uninjected paw beginning with day 16 through day 30 were computer plotted for the TB controls, the normal controls, and the drug-treated animals, and the areas under the curves [(TB controls minus normal controls) and (treated animals minus normal controls)] were determined. The results are summarized in Table III.

TABLE III

Inhibition of Uninjected Paw Volume Inflammation Days 16 through 30

| Compound of Example No. | Dose mg/kg P.O. × 29 | % Inhibition* |
|---|---|---|
| 1 | 50 | 41 |
| 2 | 50 | 81 |
| 3 | 50 | 10 |
| 4 | 50 | 23 |
| 5 | 50 | 7 |
| 6 | 50 | — |
| 7 | 50 | 30.4 |
| 8 | 50 | 4 |
| 9 | 50 | — |
| 10 | 50 | 57 |
| 11 | 50 | +19.7 |
| 12 | 50 | +4.8 |
| 13 | 50 | +8.7 |
| 14 | 50 | 6 |
| 15 | 50 | 40 |
| 16 | 50 | 18 |
| 17 | 50 | 61 |
| 18 | 50 | — |
| 19 | 50 | +20.7 |
| 20 | 50 | 36 |
| 21 | 50 | 81 |
| 22 | 50 | 1 |
| 23 | 50 | 28 |
| 24 | 50 | 0 |
| 25 | 50 | +8.5 |
| 26 | 50 | 30.4 |
| 27 | 50 | 40 |
| 28 | 50 | 72 |
| 29 | 50 | 49.0 |
| 30 | 50 | 44.1 |
| 31 | 50 | 28.9 |
| 32 | 50 | 48.6 |
| 33 | 50 | 30.1 |
| 34 | 50 | +1.6 |
| 35 | 75 | 86 |
| 36 | 50 | — |
| 37 | 50 | 37.6 |
| 38 | 50 | 1.8 |
| 39 | 50 | 2 |
| 40 | 50 | 23 |
| 41 | 50 | 27 |
| 42 | 50 | — |
| 43 | 50 | 36 |
| 44 | 50 | 15 |
| 45 | 50 | 36 |
| 46 | 50 | 9 |
| 47 | 50 | 69.3 |
| 47 | 25 | 57.7 |
| 49 | 50 | 36 |
| 50 | 50 | 62 |
| 51 | 25 | 39 |
| 52 | 25 | 45 |
| 54 | 50 | 37.6 |
| 55 | 50 | 96.2 |
| 56 | 50 | 36.2 |
| 57 | 50 | 35.5 |
| 58 | 50 | 38.2 |
| 59 | 50 | 44.1 |
| 60 | 50 | 16.9 |
| 61 | 50 | 19.8 |
| 62 | 50 | 40.6 |
| 63 | 50 | 5.3 |

TABLE III-continued

Inhibition of Uninjected Paw Volume Inflammation
Days 16 through 30

| Compound of Example No. | Dose mg/kg P.O. × 29 | % Inhibition* |
|---|---|---|
| 64 | 50 | 11.2 |
| 65 | 50 | 9.8 |
| 66 | 50 | 5.5 |
| 68 | 50 | 26.1 |
| 70 | 50 | 6.5 |
| 73 | 50 | 48.2 |

*% inhibition is the difference of the areas under the curves (AUC) of the mean uninjected paw volumes plotted for days 16, 18, 21, 23, 25, 28 and 30 according to the following formula:

$$\% \text{ inhibition} = \left[1 - \frac{(\text{Drug treated AUC}) - (\text{normal control AUC})}{(\text{TB control AUC}) - (\text{normal control AUC})}\right] \times 100$$

Lipoidal Amine-Induced Arthritis Assay

Compounds were tested for their ability to alter hind paw swelling in rats having lipoidal amine-induced arthritis. Lipoidal amine-induced arthritis was induced in Male Lewis rats (Sprague Dawley; 200–220 g) in the following manner. The test animals were divided into groups of 5 and housed in hanging cages with food and water ad libitum. On the first test day each rat is injected with 75 mg of lipoidal amine subcutaneously at the base of the tail. On the tenth day after lipoidal amine administration, each animal is weighed and test compound administration is started.

Each compound to be tested was suspended in carboxymethylcellulose (1%) and administered p.o. to the test animals in daily doses for five days (days 10–14). No dosing occurred on the fifteenth day. On day sixteen the animals were weighed again and hind paw volumes were measured using a water manometer. The hind paw volumes obtained were then compared with the hind paw volumes obtained from control test animals (lipoidal amine arthritis induced and no test compound administered) in order to determine the percentage difference between control and test animals.

The results of testing the compounds of the present invention in the lipoidal amine-induced arthritis assay are summarized in Table IV, below. The % inhibition was calculated according to the following formula:

$$\% \text{ inhibition} = \frac{Vt}{Vc} \times 100$$

where Vt is the hindpaw volume of a compound-treated animal (test group) and Vc is the hindpaw volume of a non-compound treated animal (control group).

TABLE IV

Inhibition of Lipoidal Amine-Induce Arthritis

| Compound of Example No. | Dose mg/kg p.o. × 5 | % Inhibition |
|---|---|---|
| 6 | 25 | 31 |
| 47F | 40 | 42 |

Compounds of Formula III have also been shown to prevent ischemia-induced neuronal cell damage as demonstrated in the following test system.

Stroke Model in Rats

Strokes were produced in rats by occluding the four arteries that supply blood to the brain according to the following procedure. Male Wistar rats were anesthetized with Metofane and placed into a stereotaxic instrument. A longitudinal incision was made on the dorsal surface of the neck. The neck muscles were reflected to expose the dorsal surface of the spinal column. The two vertebral arteries were exposed where they pass through the first cervical vertebra. Both arteries were permanently occluded by the application of electrocautery. After coagulation of the vertebral arteries, the rat was removed from the stereotaxic instrument and the surgical wound was sutured. Two longitudinal incisions were then made on the ventral surface of the neck. The two common carotid arteries were exposed and dissected free from surrounding nerves and connective tissue. An atraumatic clasp, fabricated mainly from silicon rubber tubing, was placed around each carotid artery in a manner such that the vessel was not traumatized or occluded. The surgical wounds were then closed. The atraumatic clasps were designed in such a manner that they could be tightened to occlude the carotid arteries by pulling on a small silastic thread that was allowed to protrude from the wound. Circulation to the brain through the carotids could be restored by relieving the tension on the silastic threads. After the surgery, the rats were allowed to recover for 24 hours.

On the day of testing, compounds were suspended in 2% acacia and were administered orally at various times before stroke induction. Strokes (cerebral ischemia) were induced by tightening the clasps around the carotids for a period of 30 minutes. During this time, rats in which strokes had successfully been produced lost the righting reflex and became unresponsive to stimuli. After 30 minutes of ischemia, tension on the clasps was removed and blood flow to the brain restored. Rats were again treated with compounds on the morning after the stroke. On the third day after the stroke the animals received an overdose of barbiturate anesthetic, and the brain was perfused in situ with 10% neutral, buffered formalin. After perfusion with amounts of formalin adequate to fix the brain, the brains were removed and stored in 10% formalin until histological sections could be prepared.

One of the areas of the brain that is most susceptible to ischemia induced damage both in the rat and the human is the $CA_1$ pyramidal cell layer of the hippocampus. In animals that remain unresponsive for the 30 minute period of ischemia, the $CA_1$ pyramidal cell layer is completely destroyed. This layer of cells was examined microscopically in histological sections prepared from the hippocampus. Brain damage was rated according to the following scale:

0 = no damage, completely intact cell layer
1 = mild damage, one-third of $CA_1$ layer dead
2 = moderate damage, two-thirds of $CA_1$ layer dead
3 = severe damage, complete destruction of $CA_1$ layer Damage in 10–12 sections from each brain was assessed in order to obtain an accurate estimate of damage. An average damage score was calculated for each treatment group. Scores from treated groups were compared statistically with scores from control groups which received only the vehicle (2% acacia) that was used to suspend the compounds. The level of significance was determined using Student's "t-test". Results are summarized in Table V.

TABLE V

Prevention of ischemia-induced brain damage in the hippocampal CA₁ region in rats

| Treatment | Dose* | No. of Rats | Damage Score** |
|---|---|---|---|
| Vehicle control | — | 6 | 2.5 ± 0.2 |
| Example 2 | 50 | 10 | 1.2 ± 0.2 ($p < 0.02$) |
| Vehicle control | — | 4 | 2.3 ± 0.8 |
| Example 2 | 200 | 6 | 0.2 ± 0.2 ($p < 0.02$) |
| Vehicle control | — | 10 | 2.5 ± 0.2 |
| Example 2 | 500 | 7 | 0.07 ± 0.007 ($p < 0.001$) |
| Vehicle control | — | 3 | 2.8 ± 0.2 |
| Example 2 | 500 | 4 | 0.0 ($p < 0.001$) |
| Vehicle control | — | 6 | 2.8 ± 0.2 |
| Example 5 | 100 | 8 | 1.8 ± 0.4 ($p = 0.05$) |
| Vehicle control | — | 8 | 2.8 ± 0.1 |
| Example 6 | 100 | 11 | 2.5 ± 0.2 |
| Vehicle control | — | 10 | 2.5 ± 0.3 |
| Example 7 | 100 | 9 | 2.5 ± 0.2 |
| Vehicle control | — | 4 | 2.5 ± 0.26 |
| Example 10*** | 100 | 4 | 0.75 ± 0.26 ($p < 0.02$) |
| Vehicle control | — | 8 | 2.7 ± 0.1 |
| Example 11 | 100 | 5 | 2.1 ± 0.3 |
| Vehicle control | — | 8 | 2.2 ± 0.3 |
| Example 12 | 100 | 8 | 1.8 ± 0.4 |
| Vehicle control | — | 12 | 2.2 ± 0.3 |
| Example 13 | 100 | 12 | 2.1 ± 0.3 |
| Vehicle control | — | 10 | 2.3 ± 0.4 |
| Example 21 | 50 | 11 | 1.9 ± 0.3 |
| Vehicle control | — | 10 | 2.7 ± 0.2 |
| Example 22 | 100 | 10 | 2.3 ± 0.3 |
| Vehicle control | — | 10 | 2.7 ± 0.2 |
| Example 23 | 100 | 9 | 2.2 ± 0.4 |
| Vehicle control | — | 8 | 2.7 ± 0.1 |
| Example 26 | 100 | 8 | 1.9 ± 0.4 |
| Vehicle control | — | 9 | 2.4 ± 0.3 |
| Example 28 | 50 | 9 | 1.0 ± 0.4 ($p = 0.009$) |
| Vehicle control | — | 8 | 2.2 ± 0.3 |
| Example 35 | 100 | 9 | 0.9 ± 0.4 ($p < 0.001$) |
| Vehicle control | — | 11 | 2.3 ± 0.3 |
| Example 36 | 100 | 7 | 2.3 ± 0.4 |
| Vehicle control | — | 8 | 2.7 ± 0.4 |
| Example 38 | 200 | 11 | 1.6 ± 0.04 |
| Vehicle control | — | 10 | 2.6 ± 0.2 |
| Example 63 | 50 | 11 | 1.7 ± 0.3 ($p = 0.03$) |
| Vehicle control | — | 9 | 2.4 ± 0.3 |
| Example 64 | 100 | 10 | 1.2 ± 0.3 ($p < 0.05$) |
| Vehicle control | — | 10 | 2.5 ± 0.3 |
| Example 69 | 100 | 10 | 1.4 ± 0.3 ($p < 0.05$) |
| Vehicle control | — | 10 | 2.28 ± 0.2 |
| Example 71 | 50 | 8 | 0.98 ± 0.42 ($p = 0.037$) |
| Vehicle control | — | 8 | 2.2 ± 0.4 |
| Example 72 | 100 | 6 | 0.7 ± 0.4 ($p = 0.039$) |

*mg/kg given orally as a suspension in 2% acacia
**mean ± standard error
***Three rats showed no damage, one rat died and was revived; $p < 0.02$.

Compounds of Formula IV have also been shown to prolong the lifespan of dystrophic mammals as demonstrated in the following test system.

Muscular Dystrophy Animal Model

Dystrophic mice (dy/dy) were obtained from Jackson Laboratories after weaning (approximately 21 days) and treatment with the compounds shown in Table VI was begun at the first sign of dystrophy. The compounds that were tested were administered in the diet and lifespan was measured during the course of treatment. The food and water sources were located in different parts of the cage requiring the animals to walk from the food source to the water source to survive. The results are shown in Table VI.

TABLE VI

Life Span Measurements of Dystrophic Mice

| Treatment | No. of Mice | Concentration[a] | Average Life Span[b] |
|---|---|---|---|
| Control | 6 | | 86 |
| Example 2 | 6 | 0.3 | 74 |
| Control | 6 | | 46 |
| Example 2 | 6 | 0.1 | 108 |
| Control | 5 | | 38 |
| Example 2 | 5 | 0.08 | 73 |
| Control | 5 | | 56 |
| Example 2 | 5 | 0.08 | 116 |
| Control | 6 | | 55 |
| Example 2 | 6 | 0.03 | 57 |
| Control | 6 | | 86 |
| Example 10 | 6 | 0.3 | 83 |
| Control | 8 | | 54 |
| Example 10 | 8 | 0.08 | 45 |
| Control | 7 | | 62 |
| Example 10 | 7 | 0.08 | 67 |
| Control | 6 | | 55 |
| Example 10 | 6 | 0.03 | 110 |
| Control | 6 | | 58 |
| Example 10 | 11 | 0.03 | 93 |
| Control | 4 | | 83 |
| Example 10 | 4 | 0.03 | 112 |
| Control | 8 | | 54 |
| Example 10 | 8 | 0.03 | 90 |
| Control | 6 | | 43 |
| Example 10 | 6 | 0.03 | 80 |
| Control | 7 | | 83 |
| Example 17 | 8 | 0.03 | 112 |
| Control | 6 | | 94 |
| Example 21 | 6 | 0.03 | 151 |
| Control | 7 | | 73 |
| Example 35 | 7 | 0.05 | 107 |

[a]Concentration (percent by weight) of compound tested in diet
[b]Expressed in days As noted above, the compounds of the present invention are physiologically active thereby lending themselves to valuable therapeutic methods as claimed herein. The methods include administering to a mammal in need thereof an effective amount of one or more compounds of the present invention sufficient for the therapeutic or prophylactic intervention desired. Such administration is accomplished by means of pharmaceutical compositions which are prepared by techniques well known in the pharmaceutical sciences. Accordingly, the present invention is also directed to pharmaceutical compositions which include at least one compound described herein in association with one or more pharmaceutically acceptable diluents, excipients or carriers.

In making the pharmaceutical compositions of the present invention, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The compounds of the present invention are effective over a wide dosage range for the indications for which they are administered. Thus, as used herein, the term "effective amount" refers to a dosage range of from about 0.5 to about 200 mg/kg of body weight per day. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingredients any of the compounds of Formula II. The examples are illustrative only and are not intended to limit the scope of the invention in any way.

EXAMPLE 74

Hard gelatin capsules are prepared using the following ingredients:

|  | Quantity (mg/capsule) |
| --- | --- |
| 5-{[3,5-bis(1,1-dimethyl-ethyl)-4-hydroxyphenyl]-methyl}-2-thioxo-4-thiazolidinone | 250 |
| Starch dried | 200 |
| Magnesium stearate | 10 |

The above ingredients are mixed and filled into hard gelatin capsules in 460 mg quantities.

EXAMPLE 75

A tablet formula is prepared using the ingredients below:

|  | Quantity (mg/tablet) |
| --- | --- |
| 5-{[3,5-bis(1,1-dimethyl-ethyl)-4-hydroxyphenyl-methylene}-4-thiazolidinone | 250 |
| Cellulose, microcrystalline | 400 |
| Silicon dioxide, fumed | 10 |

-continued

|  | Quantity (mg/tablet) |
| --- | --- |
| Stearic acid | 5 |

The components are blended and compressed to form tablets each weighing 665 mg.

EXAMPLE 76

An aerosol solution is prepared containing the following components:

|  | Weight % |
| --- | --- |
| 5-{[3,5-bis(1,1-dimethylethyl)-4-hydroxyphenyl]methyl}-4-thiazolidinone | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 77

Tablets each containing 60 mg of active ingredient are made up as follows:

| 5-{[3,5-bis(1,1-dimethyl-ethyl)-4-hydroxyphenyl]-methylene]-2-thioxo-4-thiazolidinone | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 78

Capsules each containing 80 mg of medicament are made as follows:

| 4-{[3,5-bis(1,1-dimethylethyl)-4-hydroxyphenyl]methyl}1,3-oxothiolan-5-one | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 79

Suppositories each containing 225 mg of active ingredient are made as follows:

| | |
|---|---|
| 5-{[3,5-bis(1,1-dimethylethyl)-4-hydroxyphenyl]methyl}-2-methyl-2-thioxo-4-thiazolidinone | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 80

Suspensions each containing 50 mg of medicament per 5 ml dose are made as follows:

| | |
|---|---|
| 4-{[3,5-bis(1,1-dimethylethyl)-4-hydroxyphenyl]methylene}-2-thioxo-1,3-oxothiolan-5-one | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 81

Capsules each containing 150 mg of medicament are made as follows:

| | |
|---|---|
| 5-{[3,5-bis(1,1-dimethylethyl)-4-hydroxyphenyl]methylene}-4-thiazolidinone | 150 mg |
| Starch | 164 mg |
| Microcyrstalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

I claim:

1. A compound of the formula (I):

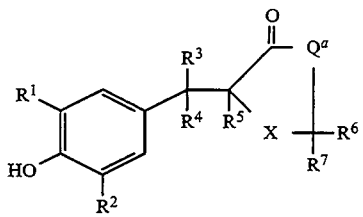

wherein:
$R^1$ and $R^2$ are each independently hydrogen, $C_1$-$C_6$ alkyl, $C_1$-$C_6$ alkoxy or

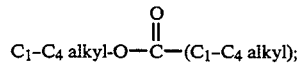

$R^3$ is hydrogen or $C_1$-$C_6$ alkyl;
$R^4$ and $R^5$ are each hydrogen, or when taken together form a bond;
$R^6$ and $R^7$ are each hydrogen;
X is

where m is 0, 1 or 2; and
Q is $NR^8$ where $R^8$ is $C_2$-$C_6$ alkenyl, $C_3$-$C_8$ cycloalkyl, $-SO_2CH_3$ or $-(CH_2)_n-Y$, where n is an integer from 0 to 3, both inclusive, and Y is cyano, $OR^9$,

tetrazolyl, $-NR^{11}R^{12}$, $-SH$, $-S(C_1$-$C_4$ alkyl) or

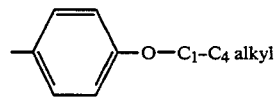

where $R^9$ is hydrogen, $C_1$-$C_4$ alkyl, tosyl or

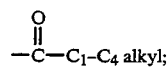

$R^{10}$ is $C_1$-$C_4$ alkoxy or $NH_2$; $R^{11}$ and $R^{12}$ are each independently hydrogen, $C_1$-$C_6$ alkyl, $C_2$-$C_6$ alkenyl, $C_2$-$C_6$ alkynyl, $-(CH_2)_qOH$, $-(CH_2)_qN(C_1$-$C_4$ alkyl)$_2$, $-(CH_2)_qS(C_1$-$C_4$ alkyl) or

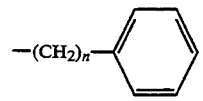

where q is an integer from 1 to 6, both inclusive, and n is as defined above, or $R^{11}$ and $R^{12}$ taken together form a morpholinyl, piperidinyl, piperazinyl or N-methylpiperazinyl ring.

2. A compound of claim 1 wherein said compound is a racemate or isomer of a compound of claim 1.

3. A compound of claim 2 wherein said compound is an isomer.

4. The compound of claim 1 wherein $R^1$ and $R^2$ are each $C_1$-$C_6$ alkyl; $R^3$ is hydrogen; $R^4$ and $R^5$ taken together form a bond; $R^6$ and $R^7$ are each hydrogen; X is

where m is 0; and Q is $NR^8$, where $R^8$ is as defined in claim 1.

5. The compound of claim 4 wherein $R^1$ and $R^2$ are each 1,1-dimethylethyl; $R^3$ is hydrogen; $R^4$ and $R^5$ taken together form a bond; $R^6$ and $R^7$ are each hydrogen; X is

where m is 0; and Q is $NR^8$, where $R^8$ is —$(CH_2)_n$—Y, where n and Y are as defined in claim 1.

6. The compound of claim 5 which is 5-{[3,5-bis(1,1-dimethylethyl)-4-hydroxyphenyl]methylene}-3-[2-(methylamino)ethyl]-4-thiazolidinone.

7. The compound of claim 5 which is 5-{[4-hydroxy-3,5-bis(1,1-dimethylethyl)phenyl]methylene}-3-dimethylamino-4-thiazolidinone.

8. The compound of claim 5 which is 5-{[3,5-bis(1,1-dimethylethyl)-4-hydroxyphenyl]methylene}-3-(2-hydroxyethyl)-4-thiazolidinone.

9. The compound of claim 5 which is 5-{[3,5-bis(1,1-dimethylethyl)-4-hydroxyphenyl]methylene}-3-(methylamino)-4-thiazolidinone.

10. The compound of claim 5 which is 3-amino-5-{[3,5-bis(1,1-dimethylethyl)-4-hydroxyphenyl]methylene}-4-thiazolidinone.

11. The compound of claim 5 which is 5-{]4-hydroxy-3,5-bis(1,1-dimethylethyl)phenyl]methylene}-3-(propylamino)-4-thiazolidinone.

12. The compound of claim 5 which is 5-{[4-hydroxy-3,5-bis(1,1-dimethylethyl)phenyl]methylene}-3-(ethylamino)-4-thiazolidinone.

13. The compound of claim 5 which is 5-{[3,5-bis(1,1-dimethylethyl)-4-hydroxyphenyl]methylene}-3-(2-aminoethyl)-4-thiazolidinone.

14. The compound of claim 5 which is 5-{[3,5-bis(1,1-dimethylethyl)-4-hydroxyphenyl]methylene}-3-[2-(dimethylamino)ethyl]-4-thiazolidinone.

15. The compound of claim 5 which is 5-{[3,5-bis(1,1-dimethylethyl)-4-hydroxyphenyl]methylene}-3-ethylmethylamino)-4-thiazolidinone.

16. The compound of claim 5 which is 5-{[3,5-bis(1,1-dimethylethyl)-4-hydroxyphenyl]methylene}-3-[2-(methylthio)ethyl]-4-thiazolidinone.

17. The compound of claim 5 which is 5-{[3,5-bis(1,1-dimethylethyl)-4-hydroxyphenyl]methylene}-3-[(2-hydroxyethyl)amino]-4-thiazolidinone.

18. A compound of the formula (I):

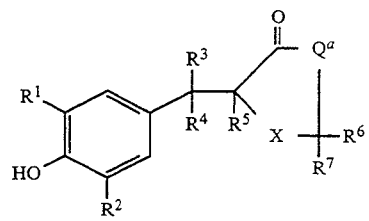

wherein:

$R^1$ and $R^2$ are each independently hydrogen, $C_1$-$C_6$ alkoxy, methyl, ethyl, hexyl, isohexyl, neohexyl or

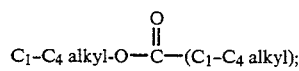

$R^3$ is hydrogen or $C_1$-$C_6$ alkyl;
$R^4$ and $R^5$ are each hydrogen, or when taken together form a bond;
$R^6$ and $R^7$ are each hydrogen;
X is

where m is 0, 1 or 2; and
Q is $NR^8$ where $R^8$ is hydrogen, $C_1$-$C_6$ alkyl, $C_2$-$C_6$ alkenyl, $C_3$-$C_8$ cycloalkyl, —$SO_2CH_3$ or —$(CH_2)_n$—Y, where n is an integer from 0 to 3, both inclusive, and Y is cyano, $OR^9$,

tetrazolyl —$NR^{11}R^{12}$, —SH, —$S(C_1$-$C_4$ alkyl) or

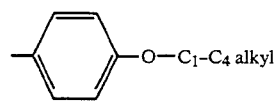

where $R^9$ is hydrogen, $C_1$-$C_4$ alkyl, tosyl or

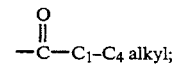

$R^{10}$ is $C_1$-$C_4$ alkoxy or $NH_2$; $R^{11}$ and $R^{12}$ are each independently hydrogen, $C_1$-$C_6$ alkyl, $C_2$-$C_6$ alkenyl, $C_2$-$C_6$ alkynyl, —$(CH_2)_qOH$, —$(CH_2)_qN(C_1$-$C_4$ alkyl)$_2$, —$(CH_2)_qS(C_1$-$C_4$ alkyl) or

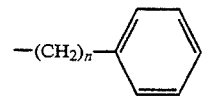

where q is an integer from 1 to 6, both inclusive, and n is as defined above, or $R^{11}$ and $R^{12}$ taken together form a morpholinyl, piperidinyl, piperazinyl or N-methylpiperazinyl ring.

19. A compound of the formula (I):

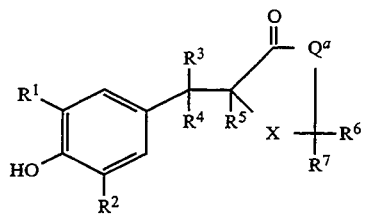

wherein:
$R^1$ and $R^2$ are each independently hydrogen, $C_1$-$C_6$ alkyl, $C_1$-$C_6$ alkoxy or

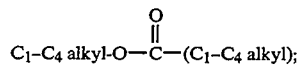

$R^3$ is hydrogen or $C_1$-$C_6$ alkyl;
$R^4$ and $R^5$ are each hydrogen, or when taken together form a bond;
$R^6$ and $R^7$ are each hydrogen;
X is

where m is 1 or 2; and
Q is $NR^8$ where $R^8$ is hydrogen, $C_1$-$C_6$ alkyl, $C_2$-$C_6$ alkenyl, $C_3$-$C_8$ cycloalkyl, $-SO_2CH_3$ or $-(CH_2)_n-Y$, where n is an integer from 0 to 3, both inclusive, and Y is cyano, $OR^9$,

tetrazolyl, $-NR^{11}R^{12}$, $-SH$, $-S(C_1$-$C_4$ alkyl) or

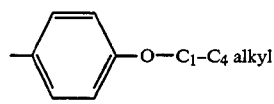

where $R^9$ is hydrogen, $C_1$-$C_4$ alkyl, tosyl or

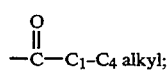

$R^{10}$ is $C_1$-$C_4$ alkoxy or $NH_2$;
$R^{11}$ and $R^{12}$ are each independently hydrogen, $C_1$-$C_6$ alkyl, $C_2$-$C_6$ alkenyl, $C_2$-$C_6$ alkynyl, $-(CH_2)_qOH$, $-(CH_2)_qN(C_1$-$C_4$ alkyl$)_2$, $-(CH_2)_qS(C_1$-$C_4$ alkyl) or

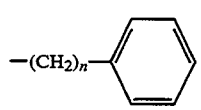

where q is an integer from 1 to 6, both inclusive, and n is as defined above, or $R^{11}$ and $R^{12}$ taken together form a morpholinyl, piperidinyl, piperazinyl or N-methylpiperazinyl ring.

20. A compound of the formula (I)

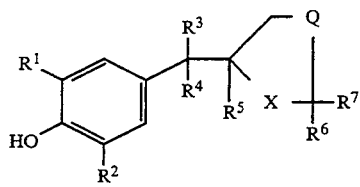

wherein:
$R^1$ and $R^2$ are both 1,1-dimethylethyl; $R^3$ is hydrogen; $R^4$ and $R^5$ are each hydrogen, or when taken together form a bond; $R^6$ and $R^7$ are each hydrogen; X is

where m is 0; and Q is $NR^8$ where $R^8$ is hydrogen or $C_1$-$C_4$ alkyl.

21. The compound of claim 1 which is 5-{[3,5bis(1,1-dimethylethyl)-4-hydroxyphenyl]methyl}-4-thiazolidinone.

22. The compound of claim 20 which is 5-{[3,5-bis(1,1-dimethylethyl)-4-hydroxyphenyl]methylene}-4-thiazolidinone.

23. The compound of claim 20 which is 5-{[3,5-bis(1,1-dimethylethyl)-4-hydroxyphenyl]methylene}-3-methyl-4-thiazolidinone.

24. A pharmaceutical composition comprising an effective amount of a compound of the formula (II)

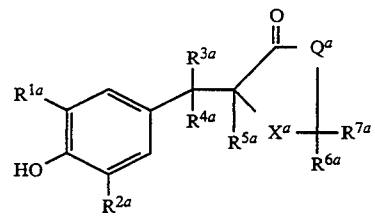

wherein:
$R^{1a}$ and $R^{2a}$ are each independently hydrogen, $C_1$-$C_6$ alkyl, $C_1$-$C_6$ alkoxy or

$R^{3a}$ is hydrogen or $C_1$-$C_6$ alkyl;
$R^{4a}$ and $R^{5a}$ are each hydrogen, or when taken together form a bond;
$R^{6a}$ and $R^{7a}$ are each hydrogen;
$X^a$ is

where m is 0, 1 or 2; and
$Q^a$ is $NR^{8a}$ where $R^{8a}$ is $C_2$-$C_6$ alkenyl, $C_3$-$C_8$ cycloalkyl, $-SO_2CH_3$ or $-(CH_2)_n-Y^a$, where n is an integer from 0 to 3, both inclusive, and $Y^a$ is cyano, $OR^{9a}$,

tetrazolyl, $-NR^{11a}R^{12a}$, $-SH$, $-S(C_1-C_4\text{alkyl})$ or

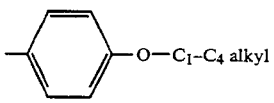

where $R^{9a}$ is hydrogen, $C_1-C_4$ alkyl or

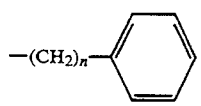

$R^{10a}$ is $C_1-C_4$ alkoxy or $NH_2$; $R^{11a}$ and $R^{12a}$ are each independently hydrogen, $C_1-C_6$ alkyl, $C_2-C_6$ alkenyl, $C_2-C_6$ alkynyl, $-(CH_2)_qOH$, $-(CH_2)_qN(C_1-C_4\text{ alkyl})_2$, $-(CH_2)_qS(C_1-C_4\text{ alkyl})$ or

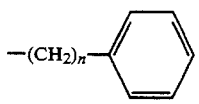

q is an integer from 1 to 6, both inclusive, and n is as defined above, or $R^{11a}$ and $R^{12a}$ taken together form a morpholinyl, piperidinyl, piperazinyl or N-methylpiperazinyl ring, in association with one or more pharmaceutically acceptable diluents, excipients or carriers therefor.

25. A pharmaceutical composition of claim 24 wherein the active ingredient is a racemate or isomer of a compound as set forth in claim 24.

26. A pharmaceutical composition of claim 25 wherein the active ingredient is an isomer.

27. The pharmaceutical composition of claim 24 wherein $R^{1a}$ and $R^{2a}$ are each $C_1-C_6$ alkyl; $R^{3a}$ is hydrogen; $R^{4a}$ and $R^{5a}$ taken together form a bond; $R^{6a}$ and $R^7$ are each hydrogen; $X^a$ is

where m is 0; and $Q^a$ is $NR^{8a}$, where $R^{8a}$ is as defined in claim 24.

28. The pharmaceutical composition of claim 27 wherein $R^{1a}$ and $R^{2a}$ are each 1,1-dimethylethyl; $R^{3a}$ is hydrogen; $R^{4a}$ and $R^{5a}$ taken together form a bond; $R^{6a}$ and $R^{7a}$ are each hydrogen; $X^a$ is

where m is 0; and $Q^a$ is $NR^{8a}$, where $R^{8a}$ is $-(CH_2)_n-Y^a$, where n and $Y^a$ are as defined in claim 24.

29. The pharmaceutical composition of claim 28 wherein the compound employed is 5-{[3,5-bis(1,1-dimethylethyl)-4-hydroxyphenyl]methylene}-3-[2-(methylamino)ethyl]-4-thiazolidinone.

30. The pharmaceutical composition of claim 28 wherein the compound employed is 5-{[4-hydroxy-3,5-bis(1,1-dimethylethyl)phenyl]methylene}-3-dimethylamino-4-thiazolidinone.

31. The pharmaceutical composition of claim 28 wherein the compound employed is 5-{[3,5-bis(1,1-dimethylethyl)-4-hydroxyphenyl]methylene}-3-(2-hydroxyethyl)-4-thiazolidinone.

32. The pharmaceutical composition of claim 28 wherein the compound employed is 5-{[3,5-bis(1,1-dimethylethyl)-4-hydroxyphenyl]methylene}-3-(methylamino)-4-thiazolidinone.

33. The pharmaceutical composition of claim 28 wherein the compound employed is 3-amino-5-{[3,5-bis(1,1-dimethylethyl)-4-hydroxyphenyl]methylene}-4-thiazolidinone.

34. The pharmaceutical composition of claim 28 wherein the compound employed is 5-{[4-hydroxy-3,5-bis(1,1-dimethylethyl)phenyl]methylene}-3-(propylamino)-4-thiazolidinone.

35. The pharmaceutical composition of claim 28 wherein the compound employed is 5-{[4-hydroxy-3,5-bis(1,1-dimethylethyl)phenyl]methylene}-3-(ethylamino)-4-thiazolidinone.

36. The pharmaceutical composition of claim 28 wherein the compound employed is 5-{[3,5-bis(1,1-dimethylethyl)-4-hydroxyphenyl]methylene}-3-(2-aminoethyl)-4-thiazolidinone.

37. The pharmaceutical composition of claim 28 wherein the compound employed is 5-{[3,5-bis(1,1-dimethylethyl)-4-hydroxyphenyl]methylene}-3-[2-(dimethylamino)ethyl]-4-thiazolidinone.

38. The pharmaceutical composition of claim 28 wherein the compound employed is 5-{[3,5-bis(1,1-dimethylethyl)-4-hydroxyphenyl]methylene}-3-(ethylmethylamino)-4-thiazolidinone.

39. The pharmaceutical composition of claim 28 wherein the compound employed is 5-{[3,5-bis(1,1-dimethylethyl)-4-hydroxyphenyl]methylene}-3-[2-(methylthio)ethyl]-4-thiazolidinone.

40. The pharmaceutical composition of claim 28 wherein the compound employed is 5-{[3,5-bis(1,1-dimethylethyl)-4-hydroxyphenyl]methylene}-3-[(2-hydroxyethyl)amino]-4-thiazolidinone.

41. A pharmaceutical composition comprising an effective amount of a compound of the formula (II)

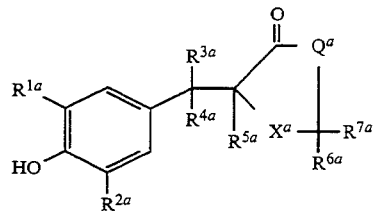

wherein:

$R^{1a}$ and $R^{2a}$ are each independently hydrogen, $C_1-C_6$ alkoxy, methyl, ethyl, hexyl, isohexyl, neohexyl or

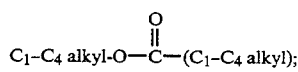

$R^{3a}$ is hydrogen or $C_1-C_6$ alkyl;

$R^{4a}$ and $R^{5a}$ are each hydrogen, or when taken together form a bond;

$R^{6a}$ and $R^{7a}$ are each hydrogen;

$X^a$ is

where m is 0, 1 or 2; and $Q^a$ is $NR^{8a}$ where $R^{8a}$ is hydrogen, $C_1$-$C_6$ alkyl, $C_2$-$C_6$ alkenyl, $C_3$-$C_8$ cycloalkyl, —$SO_2CH_3$ or —$(CH_2)_n$—$Y^a$, where n is an integer from 0 to 3, both inclusive, and $Y^a$ is cyano, $OR^{9a}$,

tetrazolyl, —$NR^{11a}R^{12a}$, —SH, —S($C_1$-$C_4$ alkyl) or

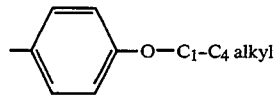

where $R^{9a}$ is hydrogen, $C_1$-$C_4$ alkyl or

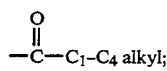

$R^{10a}$ is $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, —$(CH_2)_qOH$, —$(CH_2)_qN(C_1$-$C_4$ alkyl$)_2$, —$(CH_2)_qS(C_1$-$C_4$ alkyl) or

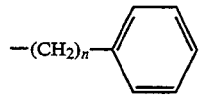

where q is an integer from 1 to 6, both inclusive, and n is as defined above, or $R^{11a}$ and $R^{12a}$ taken together form a morpholinyl, piperidinyl, piperazinyl or N-methylpiperazinyl ring, in association with one or more pharmaceutically acceptable diluents, excipients or carriers therefor.

42. A pharmaceutical composition comprising an effective amount of a compound of the formula (II)

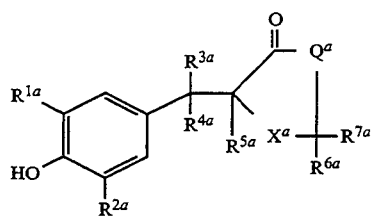

wherein:

$R^{1a}$ and $R^{2a}$ are each independently hydrogen, $C_1$-$C_6$ alkyl, $C_1$-$C_6$ alkoxy or

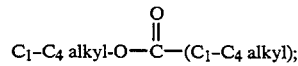

$R^{3a}$ is hydrogen or $C_1$-$C_6$ alkyl;

$R^{4a}$ and $R^{5a}$ are each hydrogen, or when taken together form a bond;

$R^{6a}$ and $R^{7a}$ are each hydrogen;

$X^a$ is

where m is 1 or 2; and $Q^a$ is $NR^{8a}$ where $R^{8a}$ is hydrogen, $C_1$-$C_6$ alkyl, $C_2$-$C_6$ alkenyl, $C_3$-$C_8$ cycloalkyl, —$SO_2CH_3$ or —$(CH_2)_n$—$Y^a$, where n is an integer from 0 to 3, both inclusive, and $Y^a$ is cyano, $OR^{9a}$,

tetrazolyl, —$NR^{11a}R^{12a}$, —SH, —S($C_1$-$C_4$ alkyl) or

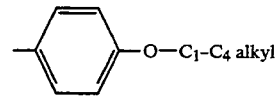

where $R^{9a}$ is hydrogen, $C_1$-$C_4$ alkyl or

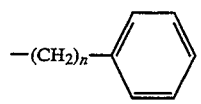

$R^{10a}$ is $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, —$(CH_2)_qOH$, —$(CH_2)_qN(C_1$-$C_4$ alkyl$)_2$, —$(CH_2)_qS(C_1$-$C_4$ alkyl) or

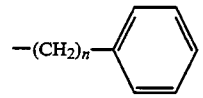

where q is an integer from 1 to 6, both inclusive, and n is as defined above, or $R^{11a}$ and $R^{12a}$ taken together form a morpholinyl, piperidinyl, piperazinyl or N-methylpiperazinyl ring, in association with one or more pharmaceutically acceptable diluents, excipients or carriers therefor.

43. A pharmaceutical composition comprising a compound of the formula (II)

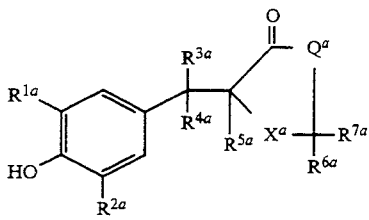

wherein:

$R^{1a}$ and $R^{2a}$ are both 1,1-dimethylethyl; $R^{3a}$ is hydrogen; $R^{4a}$ and $R^{5a}$ are each hydrogen, or when taken together form a bond; $R^{6a}$ and $R^{7a}$ are each hydrogen; $X^a$ is

where m is 0; and $Q^a$ is $NR^{8a}$, where $R^{8a}$ is hydrogen or $C_1$-$C_4$ alkyl.

44. The pharmaceutical composition of claim 43 wherein the compound employed is 5-{[3,5-bis(1,1-dimethylethyl)-4-hydroxyphenyl]methylene}-4-thiazolidinone.

45. The pharmaceutical composition of claim 43 wherein the compound employed is 5-{[3,5-bis(1,1-dimethylethyl)-4-hydroxyphenyl]methylene}-3-methyl-4-thiazolidinone.

46. A method of treating inflammation and arthritis in mammals which comprises administering to said mammal an effective amount of a compound of the formula (II)

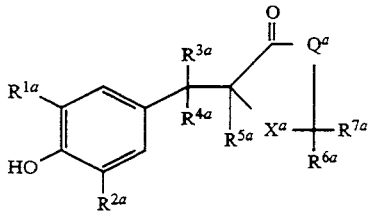

wherein:

$R^{1a}$ and $R^{2a}$ are each independently hydrogen, $C_1$-$C_6$ alkyl, $C_1$-$C_6$ alkoxy or

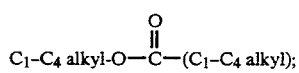

$R^{3a}$ is hydrogen or $C_1$-$C_6$ alkyl;
$R^{4a}$ and $R^{5a}$ are each hydrogen, or when taken together form a bond;
$R^{6a}$ and $R^{7a}$ are each hydrogen;
$X^a$ is

where m is 0, 1 or 2; and
$Q^a$ is $NR^{8a}$ where $R^{8a}$ is $C_2$-$C_6$ alkenyl, $C_3$-$C_8$ cycloalkyl, $-SO_2CH_3$ or $-(CH_2)_n-Y^a$, where n is an integer from 0 to 3, both inclusive, and $Y^a$ is cyano, $OR^{9a}$,

tetrazolyl, $-NR^{11a}R^{12a}$, $-SH$, $-S(C_1$-$C_4$ alkyl) or

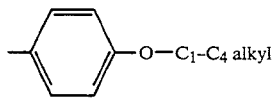

where $R^{9a}$ is hydrogen, $C_1$-$C_4$ alkyl or

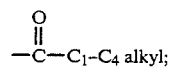

$R^{10a}$ is $C_1$-$C_4$ alkyl, $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, $-(CH_2)_qOH$, $-(CH_2)_qN(C_1$-$C_4$ alkyl$)_2$, $-(CH_2)_qS(C_1$-$C_4$ alkyl) or

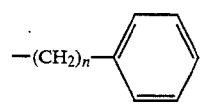

where q is an integer from 1 to 6, both inclusive, and n is as defined above, or $R^{11a}$ and $R^{12a}$ taken together form a morpholinyl, piperidinyl, piperazinyl or N-methylpiperazinyl ring.

47. A method of preventing ischemia-induced cell damage in mammals which comprises administering to said mammal an effective amount of a compound of the formula (III)

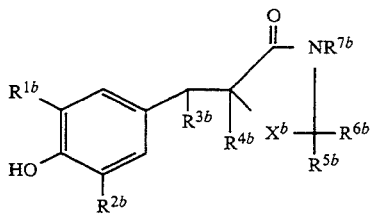

wherein:

$R^{1b}$ and $R^{2b}$ are each independently $C_1$-$C_6$ alkyl;
$R^{3b}$ and $R^{4b}$ are each hydrogen or when taken together form a bond;
$R^{5b}$ and $R^{6b}$ are both hydrogen;
$X^b$ is

where m is 0, 1 or 2; and
$R^{7b}$ is $-(CH_2)_n-Y^b$, where n is an integer from 0 to 3, both inclusive, and $Y^b$ is cyano, $OR^{8b}$,

—SH, —S($C_1$-$C_4$ alkyl), tetrazolyl, —NR$^{10b}$R$^{11b}$ or

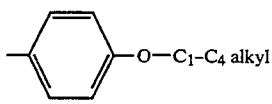

where R$^{8b}$ is hydrogen, $C_1$-$C_4$ alkyl or

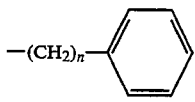

R$^{9b}$ is NH$_2$ or —OH; and R$^{10b}$ and R$^{11b}$ are each independently hydrogen, $C_1$-$C_6$ alkyl, $C_2$-$C_6$ alkenyl or $C_2$-$C_6$ alkynyl.

48. The method of claim 46 wherein R$^{1a}$ and R$^{2a}$ are each $C_1$-$C_6$ alkyl; R$^{3a}$ is hydrogen; R$^{4a}$ and R$^{5a}$ taken together form a bond; R$^{6a}$ and R$^{7a}$ are each hydrogen X$^a$ is

where m is 0; and Q$^a$ is NR$^{8a}$, where R$^{8a}$ is as defined in claim 46.

49. The method of claim 48 wherein R$^{1a}$ and R$^{2a}$ are each 1,1-dimethylethyl; R$^{3a}$ is hydrogen; R$^{4a}$ and R$^{5a}$ taken together form a bond; R$^{6a}$ and R$^{7a}$ are each hydrogen; X$^a$ is

where m is 0; and Q$^a$ is NR$^{8a}$, where R$^{8a}$ is —(CH$_2$)$_n$—Y$^a$, where n and Y$^a$ are as defined in claim 46.

50. The method of claim 49 wherein the compound employed is 5-{[3,5-bis(1,1-dimethylethyl)-4-hydroxyphenyl]methylene}-3-[2-(methylamino)ethyl]-4-thiazolidinone.

51. The method of claim 49 wherein the compound employed is 5-{[4-hydroxy-3,5-bis(1,1-dimethylethyl)-phenyl]methylene}-3-dimethylamino-4-thiazolidinone.

52. The method of claim 49 wherein the compound employed is 5-{[3,5-bis(1,1-dimethylethyl)-4-hydroxyphenyl]methylene}-3-(2-hydroxyethyl)-4-thiazolidinone.

53. The method of claim 49 wherein the compound employed is 5-{[3,5-bis(1,1-dimethylethyl)-4-hydroxyphenyl]methylene}-3-(methylamino)-4-thiazolidinone.

54. The method of claim 49 wherein the compound employed is 3-amino-5-{[3,5-bis(1,1-dimethylethyl)-4hydroxyphenyl]methylene}-4-thiazolidinone.

55. The method of claim 49 wherein the compound employed is 5-{[4-hydroxy-3,5-bis(1,1-dimethylethyl)-phenyl]methylene}-3-(propylamino)-4-thiazolidinone.

56. The method of claim 49 wherein the compound employed is 5-{[4-hydroxy-3,5-bis(1,1-dimethylethyl)-phenyl]methylene}-3-(ethylamino)-4-thiazolidinone.

57. The method of claim 49 wherein the compound employed is 5-{[3,5-bis(1,1-dimethylethyl)-4-hydroxyphenyl]methylene}-3-(2-aminoethyl)-4-thiazolidinone.

58. The method of claim 49 wherein the compound employed is 5-{[3,5-bis(1,1-dimethylethyl)-4-hydroxyphenyl]methylene}-3-[2-(dimethylamino)ethyl]-4-thiazolidinone.

59. The method of claim 49 wherein the compound employed is 5-{[3,5-bis(1,1-dimethylethyl)-4-hydroxyphenyl]methylene}-3-(ethylmethylamino)-4-thiazolidinone.

60. The method of claim 49 wherein the compound employed is 5-{[3,5-bis(1,1-dimethylethyl)-4-hydroxyphenyl]methylene}-3-[(2-hydroxyethyl)amino]-4-thiazolidinone.

61. The method of claim 47 wherein R$^{1b}$ and R$^{2b}$ are each independently $C_1$-$C_6$ alkyl; R$^{3b}$ and R$^{4b}$ taken together form a bond; R$^{5b}$ and R$^{6b}$ are each hydrogen; X$^b$ is

where m is 0; and R$^{7b}$ is as defined in claim 47.

62. The method of claim 61 wherein R$^{1b}$ and R$^{2b}$ are each 1,1-dimethylethyl; R$^{3b}$ and R$^{4b}$ taken together form a bond; R$^{5b}$ and R$^{6b}$ are each hydrogen; X$^b$ is

where m is 0; and R$^{7b}$ is —(CH$_2$)$_n$—Y$^b$, where n and Y$^b$ are as defined in claim 47.

63. The method of claim 61 wherein the compound employed is 5-{[3-(1,1-dimethylethyl)-4-hydroxy-5-methylphenyl]methylene}-3-dimethylamino-4-thiazolidinone.

64. The method of claim 62 wherein the compound employed is 5-{[3,5-bis(1,1-dimethylethyl)-4-hydroxyphenyl]methylene}-3-[2-(methylamino)ethyl]-4-thiazolidinone.

65. The method of claim 62 wherein the compound employed is 5-{[3,5-bis(1,1-dimethylethyl)-4-hydroxyphenyl]methylene}-4-oxo-3-thiazolidineacetonitrile.

66. The method of claim 62 wherein the compound employed is 5-{[4-hydroxy-3,5-bis(1,1-dimethylethyl)-phenyl]methylene}-3-dimethylamino-4-thiazolidinone.

67. The method of claim 62 wherein the compound employed is 5-{[3,5-bis(1,1-dimethylethyl)-4-hydroxyphenyl]methylene}-3-(2-hydroxyethyl)-4-thiazolidinone.

68. A method of treating inflammation and arthritis in mammals which comprises administering to said mammal an effective amount of a compound of the formula (II)

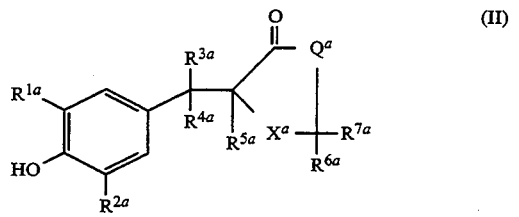

wherein:

R$^{1a}$ and R$^{2a}$ are each independently hydrogen, $C_1$-$C_6$ alkoxy, methyl, ethyl, hexyl, isohexyl, neohexyl or

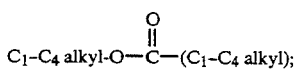

$R^{3a}$ is hydrogen or $C_1$-$C_6$ alkyl;
$R^{4a}$ and $R^{5a}$ are each hydrogen, or when taken together form a bond;
$R^{6a}$ and $R^{7a}$ are each hydrogen;
$X^a$ is

where m is 0, 1 or 2; and
$Q^a$ is $NR^{8a}$ where $R^{8a}$ is hydrogen, $C_1$-$C_6$ alkyl, $C_2$-$C_6$ alkenyl, $C_3$-$C_8$ cycloalkyl, —$SO_2CH_3$ or —$(CH_2)_n$—$Y^a$, where n is an integer from 0 to 3, both inclusive, and $Y^a$ is cyano, $OR^{9a}$,

tetrazolyl, —$NR^{11a}R^{12a}$, —SH, —$S(C_1$-$C_4$ alkyl) or

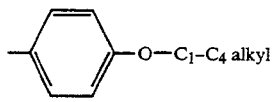

where $R^{9a}$ is hydrogen $C_1$-$C_4$ alkyl or

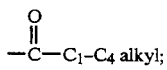

$R^{10a}$ is $C_1$-$C_4$ alkyl, $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, —$(CH_2)_qOH$, —$(CH_2)_qN(C_1$-$C_4$ alkyl)$_2$, —$(CH_2)_qS(C_1$-$C_4$ alkyl) or

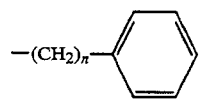

where q is an integer from 1 to 6, both inclusive, and n is as defined above, or $R^{11a}$ and $R^{12a}$ taken together form a morpholinyl, piperidinyl, piperazinyl or N-methylpiperazinyl ring.

69. A method of preventing ischemia-induced cell damage in mammals which comprises administering to said mammal an effective amount of a compound of the formula (III)

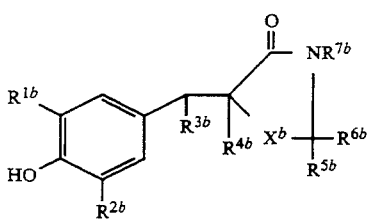

(III)

wherein:
$R^{1b}$ and $R^{2b}$ are each independently methyl, ethyl, hexyl, isohexyl or neohexyl;
$R^{3b}$ and $R^{4b}$ are each hydrogen or when taken together form a bond;
$R^{5b}$ and $R^{6b}$ are both hydrogen;
$X^b$ is

where m is 0, 1 or 2; and
$R^{7b}$ is hydrogen, $C_1$-$C_6$ alkyl or —$(CH_2)_n$—$Y^b$, where n is an integer from 0 to 3, both inclusive, and $Y^b$ is cyano, $OR^{8b}$,

—SH, —$S(C_1$-$C_4$ alkyl), tetrazolyl —$NR^{10b}R^{11b}$ or

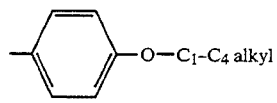

where $R^{8b}$ is hydrogen, $C_1$-$C_4$ alkyl or

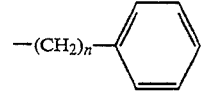

$R^{9b}$ is $NH_2$ or —OH; and $R^{10b}$ and $R^{11b}$ are each independently hydrogen, $C_1$-$C_6$ alkyl, $C_2$-$C_6$ alkenyl or $C_2$-$C_6$ alkynyl.

70. A method of treating inflammation and arthritis in mammals which comprises administering to said mammal an effective amount of a compound of the formula (II)

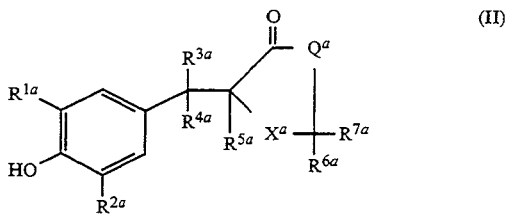

(II)

wherein:
$R^{1a}$ and $R^{2a}$ are each independently hydrogen, $C_1$-$C_6$ alkyl, $C_1$-$C_6$ alkoxy or

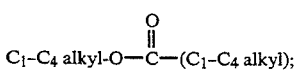

$R^{3a}$ is hydrogen or $C_1$-$C_6$ alkyl;
$R^{4a}$ and $R^{5a}$ are each hydrogen, or when taken together form a bond;
$R^{6a}$ and $R^{7a}$ are each hydrogen;
$X^a$ is

where m is 1 or 2; and $Q^a$ is $NR^{8a}$ where $R^{8a}$ is hydrogen, $C_1$-$C_6$ alkyl, $C_2$-$C_6$ alkenyl, $C_3$-$C_8$ cycloalkyl, —$SO_2CH_3$ or —$(CH_2)_n$—$Y^a$, where n is an integer from 0 to 3, both inclusive, and $Y^a$ is cyano, $OR^{9a}$,

tetrazolyl, —$NR^{11a}R^{12a}$, —SH, —S($C_1$-$C_4$ alkyl) or

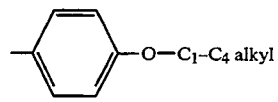

where $R^{9a}$ is hydrogen, $C_1$-$C_4$ alkyl or

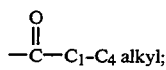

$R^{10a}$ is $C_1$-$C_4$ alkyl, $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, —$(CH_2)_qOH$, —$(CH_2)_qN(C_1$-$C_4$ alkyl$)_2$, —$(CH_2)_qS(C_1$-$C_4$ alkyl) or

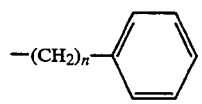

where q is an integer from 1 to 6, both inclusive, and n is as defined above, or $R^{11a}$ and $R^{12a}$ taken together form a morpholinyl, piperidinyl, piperazinyl or N-methylpiperazinyl ring.

71. A method of preventing ischemia-induced cell damage in mammals which comprises administering to said mammal an effective amount of a compound of the formula (III)

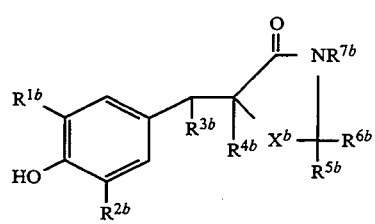

wherein:

$R^{1b}$ and $R^{2b}$ are each independently $C_1$-$C_6$ alkyl;

$R^{3b}$ and $R^{4b}$ are each hydrogen or when taken together form a bond;

$R^{5b}$ and $R^{6b}$ are both hydrogen;

$X^b$ is

where m is 1 or 2; and $R^{7b}$ is hydrogen, $C_1$-$C_6$ alkyl or —$(CH_2)_n$—$Y^b$, where n is an integer from 0 to 3, both inclusive, and $Y^b$ is cyano, $OR^{8b}$,

—SH, —S($C_1$-$C_4$ alkyl), tetrazolyl, —$NR^{10b}R^{11b}$ or

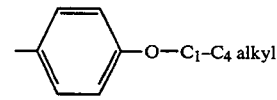

where $R^{8b}$ is hydrogen $C_1$-$C_4$ alkyl or

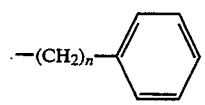

$R^{9b}$ is $NH_2$ or —OH; and $R^{10b}$ and $R^{11b}$ are each independently hydrogen, $C_1$-$C_6$ alkyl, $C_2$-$C_6$ alkenyl or $C_2$-$C_6$ alkynyl.

72. A method of preventing ischemia-induced cell damage in mammals which comprises administering to said mammal an effective amount of 5-{[4-hydroxy-3-methyl-5-(1,1-dimethylethylphenyl]methylene}-3-methyl-4-thiazolidinone.

73. A method of treating a dystrophic mammal which comprises administering to said mammal an effective amount of a compound of the formula (IV)

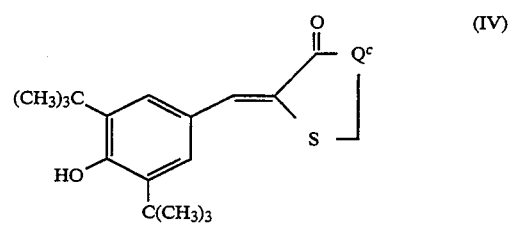

wherein:

$Q^c$ is $NR^{7c}$, where $R^{7c}$ is hydrogen, $C_1$-$C_6$ alkyl, $NR^{8c}R^{9c}$ or —$(CH_2)_n$—OH, where $R^{8c}$ and $R^{9c}$ are each independently hydrogen or $C_1$-$C_4$ alkyl and n is an integer from 0 to 3, both inclusive.

74. The method of claim 73 wherein the compound employed is 5-{[3,5-bis(1,1-dimethylethyl)-4-hydroxyphenyl]methylene}-4-thiazolidinone.

75. The method of claim 73 wherein the compound employed is 5-{[3,5-bis(1,1-dimethylethyl)-4-hydroxyphenyl]methylene}-3-methyl-4-thiazolidinone.

76. The method of claim 73 wherein the compound employed is 5-{[4-hydroxy-3,5-bis(1,1-dimethylethyl)-phenyl]methylene}-3-dimethylamino-4-thiazolidinone.

77. The method of claim 73 wherein the compound employed is 5-{[3,5-bis(1,1-dimethylethyl)-4-hydroxyphenyl]methylene}-3-(2-hydroxyethyl)-4-thiazolidinone.

78. A method of treating inflammation and arthritis in mammals which comprises administering to said mammal an effective amount of a compound of the formula (II)

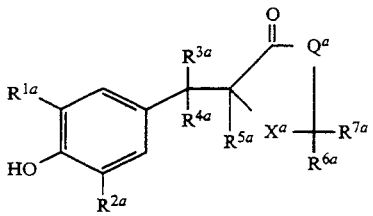

wherein:
$R^{1a}$ and $R^{2a}$ are both 1,1-dimethylethyl; $R^{3a}$ is hydrogen; $R^{4a}$ and $R^{5a}$ are each hydrogen, or when taken together form a bond; $R^{6a}$ and $R^{7a}$ are each hydrogen; $X^a$ is

where m is 0; and $Q^a$ is $NR^{8a}$, where $R^{8a}$ is hydrogen or $C_1$-$C_4$ alkyl.

79. The method of claim 78 wherein the compound employed is 5-{[3,5-bis(1,1-dimethylethyl)-4-hydroxyphenyl]methylene}-4-thiazolidinone.

80. The method of claim 78 wherein the compound employed is 5-{[3,5-bis(1,1-dimethylethyl)-4-hydroxyphenyl]methylene}-3-methyl-4-thiazolidinone.

81. A method of preventing ischemia-induced cell damage in mammals which comprises administering to said mammal an effective amount of a compound of the formula (III)

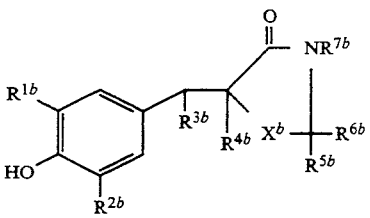

wherein:
$R^{1b}$ and $R^{2b}$ are both 1,1-dimethylethyl; $R^{3b}$ and $R^{4b}$ taken together form a bond; $R^{5b}$ and $R^{6b}$ are both hydrogen; $X^b$ is

wherein m is 0; and $R^{7b}$ is hydrogen or $C_1$-$C_4$ alkyl.

82. The method of claim 81 wherein the compound employed is 5-{[3,5-bis(1,1-dimethylethyl )-4-hydroxyphenyl]methylene}-4-thiazolidinone.

83. The method of claim 81 wherein the compound employed is 5-{[3,5-bis(1,1-dimethylethyl)-4-hydroxyphenyl]methylene}-3-methyl-4-thiazolidinone.

84. A compound of claim 20 wherein said compound is a racemate or isomer of a compound of claim 20.

85. A compound of claim 84 wherein said compound is an isomer.

86. A pharmaceutical composition of claim 43 wherein the active ingredient is a racemate or isomer of a compound as set forth in claim 43.

87. A pharmaceutical composition of claim 86 wherein the active ingredient is an isomer.

88. The compound of claim 1 wherein:
$R^1$ and $R^2$ are each independently hydrogen, $C_1$-$C_6$ alkyl, $C_1$-$C_6$ alkoxy or

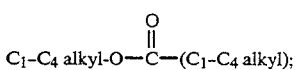

$R^3$ is hydrogen or $C_1$-$C_6$ alkyl;
$R^4$ and $R^5$ are each hydrogen, or when taken together form a bond;
$R^6$ and $R^7$ are each hydrogen;
X is

where m is 0, 1 or 2; and
Q is $NR^8$ where $R^8$ is $C_3$-$C_8$ cycloalkyl, —$SO_2CH_3$ or —$(CH_2)_n$—Y, where n is an integer from 0 to 3, both inclusive, and Y is cyano, $OR^9$,

tetrazolyl —$NR^{11}R^{12}$, —SH, —S($C_1$-$C_4$ alkyl) or

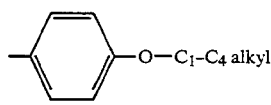

where $R^9$ is hydrogen, $C_1$-$C_4$ alkyl, tosyl or

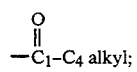

$R^{10}$ is $C_1$-$C_4$ alkoxy or $NH_2$; $R^{11}$ and $R^{12}$ are each independently hydrogen, $C_1$-$C_6$ alkyl, $C_2$-$C_6$ alkenyl, $C_2$-$C_6$ alkynyl, —$(CH_2)_qOH$, —$(CH_2)_qN(C_1$-$C_4$ alkyl$)_2$, —$(CH_2)_qS$ ($C_1$-$C_4$ alkyl ) or

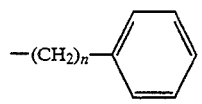

where q is an integer from 1 to 6, both inclusive, and n is as defined above, or $R^{11}$ and $R^{12}$ taken together form a morpholinyl, piperidinyl, piperazinyl or N-methylpiperazinyl ring.

89. The method of claim 46 wherein:
$R^{1a}$ and $R^{2a}$ are each independently hydrogen, $C_1$-$C_6$ alkyl, $C_1$-$C_6$ alkoxy or

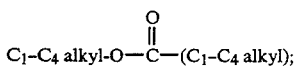

$R^{3a}$ is hydrogen or $C_1$-$C_6$ alkyl;

$R^{4a}$ and $R^{5a}$ are each hydrogen, or when taken together form a bond;

$R^{6a}$ and $R^{7a}$ are each hydrogen;

$X^a$ is

where m is 0, 1 or 2; and $Q^a$ is $NR^{8a}$ where $R^{8a}$ is $C_3$-$C_8$ cycloalkyl, $-SO_2CH_3$ or $-(CH_2)_n-Y^a$, where n is an integer from 0 to 3, both inclusive, and $Y^a$ is cyano, $OR^{9a}$,

tetrazolyl, $-NR^{11a}R^{12a}$, $-SH$, $-S(C_1$-$C_4$ alkyl ) or

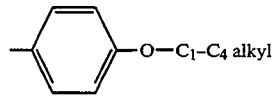

where $R^{9a}$ is hydrogen, $C_1$-$C_4$ alkyl or

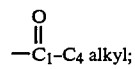

$R^{10a}$ is $C_1$-$C_4$ alkyl, $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, $-(CH_2)_qOH$, $-(CH_2)_qN(C_1$-$C_4$ alkyl$)_2$, $-(CH_2)_qS(C_1$-$C_4$ alkyl) or

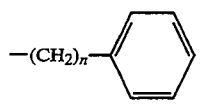

where q is an integer from 1 to 6, both inclusive, and n is as defined above, or $R^{11a}$ and $R^{12a}$ taken together form a morpholinyl, piperidinyl, piperazinyl or N-methylpiperazinyl ring.

90. The composition of claim 24 wherein:

$R^{1a}$ and $R^{2a}$ are each independently hydrogen, $C_1$-$C_6$ alkyl, $C_1$-$C_6$ alkoxy or

$R^{3a}$ is hydrogen or $C_1$-$C_6$ alkyl;

$R^{4a}$ and $R^{5a}$ are each hydrogen, or when taken together form a bond;

$R^{6a}$ and $R^{7a}$ are each hydrogen;

$X^a$ is

where m is 0, 1 or 2; and $Q^a$ is $NR^{8a}$ where $R^{8a}$ is $C_3$-$C_8$ cycloalkyl, $-SO_2CH_3$ or $-(CH_2)_n-Y^a$, where n is an integer from 0 to 3, both inclusive, and $Y^1$ is cyano, $OR^{9a}$,

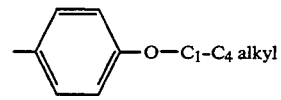

tetrazolyl, $-NR^{11a}R^{12a}$, $-SH$, $-S(C_1$-$C_4$ alkyl) or

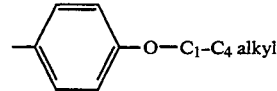

where $R^{9a}$ is hydrogen, $C_1$-$C_4$ alkyl or

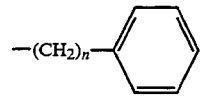

$R^{10a}$ is $C_1$-$C_4$ alkoxy or $NH_2$; $R^{11a}$ and $R^{12a}$ are each independently hydrogen, $C_1$-$C_6$ alkyl, $C_2$-$C_6$ alkenyl, $C_2$-$C_6$ alkynyl, $-(CH_2)_qOH$, $-(CH_2)_qN(C_1$-$C_4$ alkyl$)_2$, $-(CH_2)_qS(C_1$-$C_4$ alkyl ) or where q is an integer from 1 to 6, both inclusive, and n is as defined above, or $R^{11a}$ and $R^{12a}$ taken together form a morpholinyl, piperidinyl, piperazinyl or N-methylpiperazinyl ring.

* * * * *

UNITED STATES PATENT AND TRADEMARK OFFICE
CERTIFICATE OF CORRECTION

PATENT NO. : 5,356,917

DATED : October 18, 1994

INVENTOR(S) : Jill A. Panetta

It is certified that error appears in the above-indentified patent and that said Letters Patent is hereby corrected as shown below:

Claim 1, column 48, lines 1-10, the formula should read

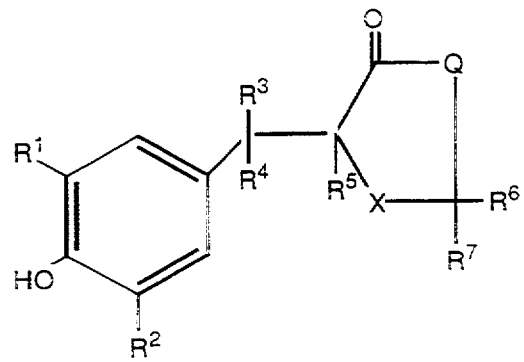

instead of

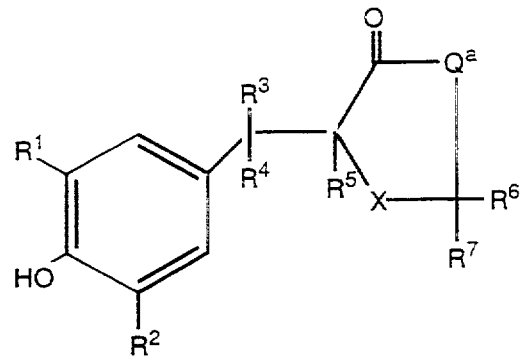

UNITED STATES PATENT AND TRADEMARK OFFICE
CERTIFICATE OF CORRECTION

PATENT NO. : 5,356,917
DATED : October 18, 1994
INVENTOR(S) : Jill A. Panetta

It is certified that error appears in the above-indentified patent and that said Letters Patent is hereby corrected as shown below:

Claim 18, column 50, lines 1-10, the formula should read

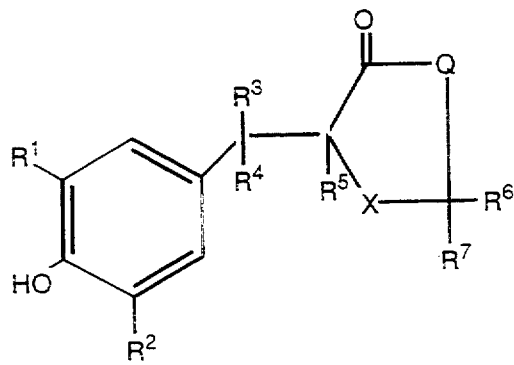

instead of

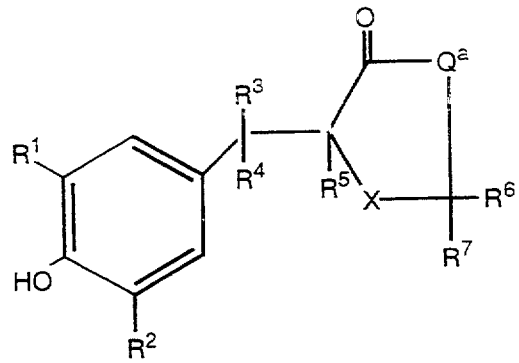

UNITED STATES PATENT AND TRADEMARK OFFICE
CERTIFICATE OF CORRECTION

PATENT NO. : 5,356,917

DATED : October 18, 1994

INVENTOR(S) : Jill A. Panetta

It is certified that error appears in the above-indentified patent and that said Letters Patent is hereby corrected as shown below:

Claim 19, column 51, lines 1-10, the formula should read

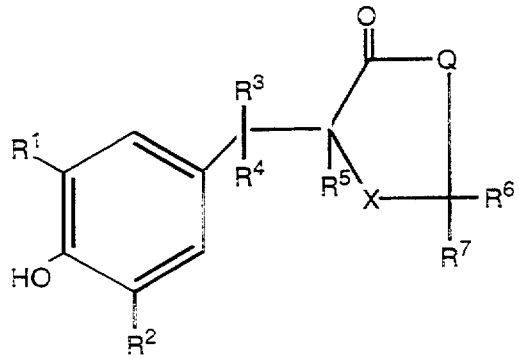

instead of

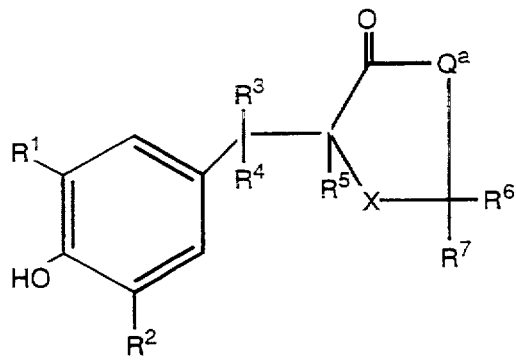

UNITED STATES PATENT AND TRADEMARK OFFICE
CERTIFICATE OF CORRECTION

PATENT NO. : 5,356,917
DATED : October 18, 1994
INVENTOR(S) : Jill A. Panetta

It is certified that error appears in the above-indentified patent and that said Letters Patent is hereby corrected as shown below:

Claim 24, column 53, lines 15-20, delete

" 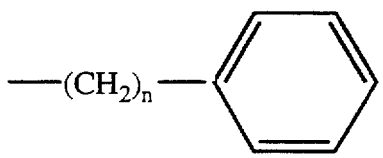 ", and insert therefor -- $-C-C_1-C_4$ alkyl -- .

Claim 24, column 53, line 32, before "q is", insert --where--.

Claim 27, column 53, line 46, delete "$R^7$", and insert therefor --$R^{7a}$--.

Claim 42, column 56, lines 40-45, delete

" 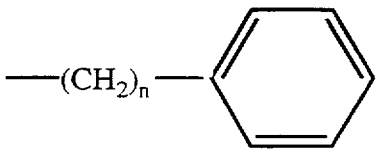 ", and insert therefor -- $-C-C_1-C_4$ alkyl -- .

Claim 47, column 59, lines 11-15, delete

" 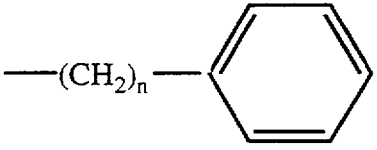 ", and insert therefor -- $-C-C_1-C_4$ alkyl -- .

UNITED STATES PATENT AND TRADEMARK OFFICE
CERTIFICATE OF CORRECTION

PATENT NO. : 5,356,917
DATED : October 18, 1994
INVENTOR(S) : Jill A. Panetta

It is certified that error appears in the above-indentified patent and that said Letters Patent is hereby corrected as shown below:

Claim 69, column 62, lines 32-37, delete

" 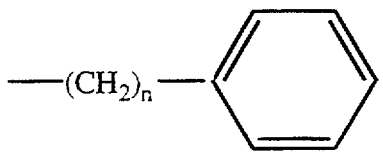 " , and insert therefor --  --.

Claim 71, column 64, lines 25-30, delete

" 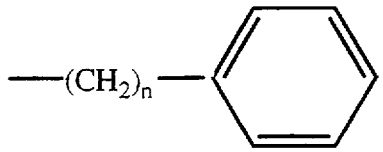 " , and insert therefor --  --.

Claim 90, column 68, line 18, delete "$Y^1$", and insert therefor --$Y^a$--.

UNITED STATES PATENT AND TRADEMARK OFFICE
CERTIFICATE OF CORRECTION

PATENT NO. : 5,356,917

DATED : October 18, 1994

INVENTOR(S) : Jill A. Panetta

It is certified that error appears in the above-indentified patent and that said Letters Patent is hereby corrected as shown below:

Claim 90, column 68, lines 34-39, delete

"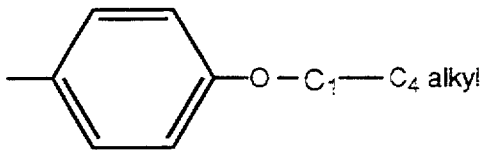, and insert therefor --  --.

Signed and Sealed this

Second Day of April, 1996

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,356,917
DATED : October 18, 1994
INVENTOR(S) : Jill A. Panetta

It is certified that error appears in the above-indentified patent and that said Letters Patent is hereby corrected as shown below:

Claim 20, column 52, lines 1-10, the formula should read

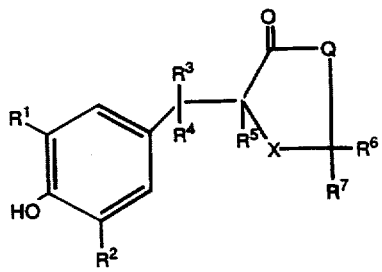

instead of

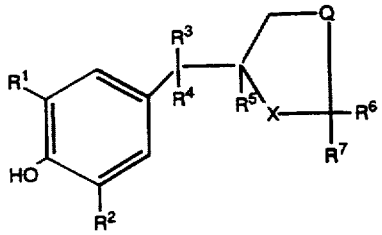

Signed and Sealed this

Twenty-first Day of May, 1996

Attest:

BRUCE LEHMAN

Attesting Officer   Commissioner of Patents and Trademarks